(12) United States Patent
Kato et al.

(10) Patent No.: US 7,632,865 B2
(45) Date of Patent: Dec. 15, 2009

(54) THIOAMIDES AND SALTS THEREOF AND CYTOKINE PRODUCTION INHIBITORS CONTAINING BOTH

(75) Inventors: Fuminori Kato, Kusatsu (JP); Hirohiko Kimura, Kusatsu (JP); Kiyoshi Tamai, Kusatsu (JP); Kazuhiro Yamamoto, Kusatsu (JP); Mitsuo Sano, Kusatsu (JP); Shinya Mori, Kusatsu (JP); Takashi Okada, Kusatsu (JP); Toshihiko Ueki, Kusatsu (JP); Kumiko Azuma, Kusatsu (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 419 days.

(21) Appl. No.: 10/588,859

(22) PCT Filed: Feb. 16, 2005

(86) PCT No.: PCT/JP2005/002348

§ 371 (c)(1),
(2), (4) Date: Aug. 9, 2006

(87) PCT Pub. No.: WO2005/077895

PCT Pub. Date: Aug. 25, 2005

(65) Prior Publication Data

US 2007/0219215 A1 Sep. 20, 2007

(30) Foreign Application Priority Data

Feb. 17, 2004 (JP) .............................. 2004-040444

(51) Int. Cl.
*A61K 31/165* (2006.01)
*C07C 327/42* (2006.01)

(52) U.S. Cl. ........................................ 514/599; 564/74

(58) Field of Classification Search ................. 514/599; 564/74
See application file for complete search history.

(56) References Cited

FOREIGN PATENT DOCUMENTS

| JP | 52 100476 | 8/1977 |
|---|---|---|
| JP | 52-100476 | 8/1977 |
| JP | 9 176100 | 7/1997 |
| JP | 2002-503723 | 2/2002 |
| JP | 2002 503723 | 2/2002 |
| JP | 2002-338537 | 11/2002 |
| JP | 2002 338537 | 11/2002 |
| JP | 2003 506466 | 2/2003 |
| JP | 2003-506466 | 2/2003 |
| WO | 02/051397 | 7/2002 |

OTHER PUBLICATIONS

Isagawa, Kakuzo et al., "N- (Chlorbenzoyl Amino Alkyl) Piperidine Rui Oyobi N- (Chlorthiobenzoyl Amino Alkyl) Piperidine rui no Gosei", Nihon Kagaku Zasshi, vol. 90, No. 10, pp. 1051 to 1053, 1969.

Strath, Malcolm et al., "Detection of Eosinophils Using an Eosinophil Peroxidase Assay. Its Use as an Assay for Eosinophil Differntiation Factors", Journal of Immunological Methods, vol. 83, pp. 209-215, 1985.

*Primary Examiner*—Taofiq A Solola
(74) *Attorney, Agent, or Firm*—Oblon, Spivak, McClelland, Maier & Neustadt, L.L.P.

(57) ABSTRACT

To provide cytokine production inhibitors useful as preventive or therapeutic medicines for diseases accompanied by hyperactivated immune functions.

A cytokine production inhibitor containing, as an active ingredient, a thioamide compound represented by the formula (I) or a salt thereof:

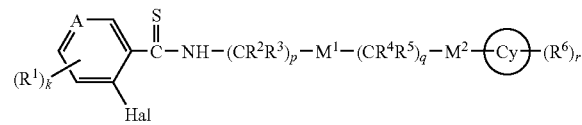

wherein A is N, NO, C—$NO_2$ or C—CN; Hal is a halogen; $M^1$ is alkyl, alkenyl, alkynyl, cycloalkyl, cycloalkenyl, aryl, heterocyclyl, amino, O, S, SO or $SO_2$; $M^2$ is amino, O, S or a single bond; $R^1$ is a halogen, alkyl or the like; each of $R^2$, $R^3$, $R^4$ and $R^5$ is independently H, alkyl or the like; $R^6$ is a halogen, alkyl or the like; Cy is cycloalkyl, cycloalkenyl, aryl or heterocyclyl; each of k, p and q is independently an integer of from 0 to 3; and r is an integer of from 0 to 5.

4 Claims, No Drawings

THIOAMIDES AND SALTS THEREOF AND CYTOKINE PRODUCTION INHIBITORS CONTAINING BOTH

TECHNICAL FIELD

The present invention relates to thioamide compounds or salts thereof, useful as preventive or therapeutic medicines for diseases accompanied by hyperactivated immune functions.

BACKGROUND ART

In immune reactions in the body, cytokines produced from various immunocytes control direction of the immune responses. In this regulation of immune responses, it is helper T cells that play a central role, and they are classified into subsets Th1 and Th2 depending upon the type of cytokines they produce. Th1 type cells are known to produce mainly e.g. interleukin 2 (IL-2) and interferon γ (IFN-γ) and to be concerned with cellular immunity such as protection against infection by e.g. virus and bacteria. Th2 type cells are known to produce mainly e.g. interleukin 4 (IL-4), interleukin 5 (IL-5), interleukin 6 (IL-6), interleukin 10 (IL-10) and interleukin 13 (IL-13) and to be concerned with humoral immunity such as protection against parasitic infection and antibody production from B cells. However, it has been clarified that if control of such biophylactic mechanism dysfunctions or deteriorates for some reason, hyperactivation or imbalance of immune function may occur, thus inducing or deteriorating various diseases.

Immune response of Th2 type induces or activates, due to its hyperactivation, allergic inflammation reactions such as immediate type allergy with which IgE antibody or mast cells are mainly concerned, and delayed-type allergy with which eosinophils are mainly concerned, and is deeply concerned with induction or deterioration of various allergic diseases such as urticaria, food allergy, anaphylactic shock, hypereosinophilic syndrome, asthma, allergic rhinitis, allergic conjunctivitis and atopic dermatitis. Further, abnormal hyperactivation of immune reaction of Th2 type is deeply concerned also with systemic autoimmune diseases in a pathophysiologic state where antibody production or humoral immunity is hyperactivated, such as systemic lupus erythematosus. It is considered to be important to control the immune response of Th2 type in order to treat or prevent such allergic diseases. On the other hand, immune response of Th1 type induces or activates cellular immune responses due to its hyperactivation, and is deeply concerned with induction or deterioration of organ specific autoimmune diseases such as chronic rheumatoid arthritis, type I diabetes, Hashimoto's thyroiditis, myasthenia gravis and multiple sclerosis. Further, cellular immune response of Th1 type is deeply concerned also with graft rejection accompanying organ transplantation. It is considered to be important to control immune response of Th1 type in order to prevent or treat such autoimmune diseases or graft rejection after transplantation.

Patent document 1 discloses amide compounds effective as cytokine production inhibitors, which, however, include no thioamide compounds.

Patent document 1: WO02/51397

DISCLOSURE OF THE INVENTION

Problems that the Invention is to Solve

At the present time, it is difficult to treat such serious immune or allergic diseases by specifically regulating immune response of Th1 or Th2 type, and immunosuppressant agents which strongly suppress production of both Th1 and Th2 type cytokines, such as cyclosporin and FK506, in addition to steroids, are mainly used as therapeutic medicines for such diseases. However, various side effects such as dysfunction of adrenal cortex, diabetes, peptic ulcer and glaucoma have been problematic with respect to steroids, and serious side effects such as damage to the kidney and the central nervous system have been problematic with respect to cyclosporin and FK506, and development of a new type of cytokine production inhibitors which are different from the above agents, has been desired.

Means of Solving the Problems

The present inventors have conducted extensive studies to find more excellent cytokine production inhibitors and, as a result, have found that specific thioamide compounds have cytokine production inhibitory effects, and the present invention has been accomplished on the basis of this discovery.

Namely, the present invention relates to a thioamide compound represented by the formula (I) or a salt thereof:

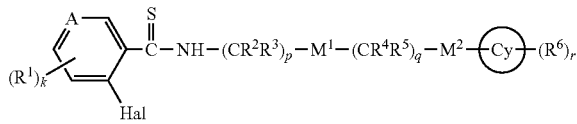

wherein A is a nitrogen atom, N-oxide, C—NO$_2$ or C—CN; Hal is a halogen atom; M$^1$ is an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted, an oxygen atom, a sulfur atom, SO or SO$_2$; M$^2$ is an amino group which may be substituted, an oxygen atom, a sulfur atom or a single bond; R$^1$ is a halogen atom, a cyano group, a nitro group, an alkyl group which may be substituted, an alkoxy group which may be substituted, an alkylthio group which may be substituted, an amino group which may be substituted or a heterocyclic group which may be substituted; each of R$^2$, R$^3$, R$^4$ and R$^5$ is independently a hydrogen atom, an alkyl group which may be substituted, a cyano group or an alkyloxycarbonyl group; R$^6$ is a halogen atom, a cyano group, a nitro group, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted or B-Q (wherein B is a carbonyl group, a carbonyloxy group, an oxycarbonyl group, an oxygen atom, a sulfur atom, SO or SO$_2$; and Q is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted or an amino group which may be substituted); Cy is a cycloalkyl group, a cycloalkenyl group, an aryl group or a heterocyclic group; each of k, p and q is independently an integer of from 0 to 3; and r is an integer of from 0 to 5, and a cytokine production inhibitor containing the same as an active ingredient.

The compounds of the formula (I) suppress production of Th2 type cytokines, whereby they are useful as preventive or therapeutic medicines for various allergic diseases such as urticaria, food allergy, anaphylactic shock, hypereosinophilic syndrome, asthma, allergic rhinitis, allergic conjunctivitis and atopic dermatitis; and systemic autoimmune diseases in which antibody production or humoral immunity is hyperactivated, such as systemic lupus erythematosus. Further, they suppress production of Th1 type cytokines, whereby they are useful as preventive or therapeutic medicines for organ specific autoimmune diseases such as chronic rheumatoid arthritis, type I diabetes, Hashimoto's thyroiditis, myasthenia gravis and multiple sclerosis; and graft rejection accompanying organ transplantation.

The salt of the compound of the above formula (I) may be any pharmaceutically acceptable salt, and it may, for example, be a mineral acid salt such as a hydrochloride, a sulfate or a nitrate; an organic acid salt such as a p-toluenesulfonate, a propanesulfonate or a methanesulfonate; an alkali metal salt such as a potassium salt or a sodium salt; an alkaline earth metal salt such as a calcium salt; or an organic amine salt such as a triethanolamine salt or a tris(hydroxymethyl)aminomethane salt.

Some of the compounds of the formula (I) or salts thereof have crystal water. Some of the compounds of the formula (I) or salts thereof have polymorphism.

Each halogen atom in the formula (I) may be a fluorine atom, a chlorine atom, a bromine atom or an iodine atom.

Each of the alkyl moiety, which is included in the definition of the substituents in the formula (I), and the alkyl moiety in each of the secondary substituent and the tertiary substituent as described hereinafter, may be usually one having a carbon number of from 1 to 20, and it may, for example, be methyl, ethyl, propyl, butyl, pentyl, hexyl, heptyl, octyl, decyl or nonadecyl, and they include linear or branched aliphatic structural isomers.

Each of the alkenyl moiety, which is included in the definition of the substitutents in the formula (I), and the alkenyl moiety in each of the secondary substituent and the tertiary substituent as described hereinafter, may be usually one having a carbon number of from 2 to 20, and it may, for example, be vinyl, propenyl, butenyl, pentenyl, hexenyl, decenyl or nonadecenyl, and they include linear or branched aliphatic structural isomers.

Each of the alkynyl moiety, which is included in the definition of the substituents in the formula (I), and the alkynyl moiety in each of the secondary substituent and the tertiary substituent as described hereinafter, may be usually one having a carbon number of from 2 to 20, and it may, for example, be ethynyl, propynyl, butynyl, pentynyl, hexynyl, decynyl or nonadecynyl, and they include linear or branched aliphatic structural isomers.

Each of the cycloalkyl moiety, which is included in the definition of the substituents in the formula (I), and the cycloalkyl moiety in each of the secondary substituent and the tertiary substituent as described hereinafter, may be usually one having a carbon number of from 3 to 10, and it may, for example, be a monocyclic group such as cyclopropyl, cyclobutyl, cyclopentyl, cyclohexyl or cyclooctyl; a fused polycyclic group; or a bridged polycyclic group such as adamantyl, noradamantyl, norbornanyl or norbornanonyl.

Each of the cycloalkenyl moiety, which is included in the definition of the substituents in the formula (I), and the cycloalkenyl moiety in each of the secondary substituent and the tertiary substituent as described hereinafter, may be usually one having a carbon number of from 3 to 10, and it may, for example, be a monocyclic group such as cyclopentenyl, cyclohexenyl or cyclooctenyl, a fused polycyclic group or a bridged polycyclic group.

Each of the aryl moiety, which is included in the definition of the substituents in the formula (I), and the aryl moiety in each of the secondary substituent and the tertiary substituent as described hereinafter, may be a fused polycyclic group such as naphthyl, as well as phenyl.

Each of the heterocyclic moiety, which is included in the definition of the substituents in the formula (I), and the heterocyclic moiety in each of the secondary substituent and the tertiary substituent as described hereinafter, may, for example, be a five-membered monocyclic heterocyclic group such as pyrrolyl, pyrrolinyl, pyrrolidinyl, furanyl, dihydrofuranyl, tetrahydrofuranyl, thienyl, dihydrothienyl, tetrahydrothienyl, pyrazolyl, pyrazolinyl, pyrazolidinyl, imidazolyl, imidazolinyl, imidazolidinyl, oxazolyl, oxazolinyl, oxazolidinyl, isoxazolyl, isoxazolinyl, isoxazolidinyl, thiazolyl, thiazolinyl, thiazolidinyl, isothiazolyl, isothiazolinyl, isothiazolidinyl, oxadiazolyl, oxadiazolinyl, oxadiazolidinyl, thiadiazolyl, thiadiazolinyl, thiadiazolidinyl, triazolyl, triazolinyl, triazolidinyl, tetrazolyl, tetrazolinyl, tetrazolidinyl, dioxolyl, dioxolanyl, dithiolyl or dithiolanyl; a six-membered monocyclic heterocyclic group such as pyridyl, dihydropyridyl, tetrahydropyridyl, piperidinyl, pyrimidyl, dihydropyrimidyl, tetrahydropyrimidyl, hexahydropyrimidyl, pyridazinyl, dihydropyridazinyl, tetrahydropyridazinyl, hexahydropyridazinyl, pyrazinyl, dihydropyrazinyl, tertahydropyrazinyl, piperazinyl, triazinyl, dihydrotriazinyl, tetrahydrotriazinyl, hexahydrotriazinyl, pyranyl, dihydropyranyl, tetrahydropyranyl, dioxinyl, dioxenyl, dioxanyl, dithianyl or morpholinyl; a fused polycyclic heterocyclic group such as thienothienyl, dihydrocyclopentathienyl, indolyl, tetrahydroindolyl, isoindolyl, tetrahydroisoindolyl, benzothienyl, tetrahydrobenzothienyl, benzofuranyl, tetrahydrobenzofuranyl, benzoxazolyl, tetrahydrobenzoxazolyl, benzisoxazolyl, tetrahydrobenzisoxazolyl, benzothiazolyl, tetrahydrobenzothiazolyl, benzisothiazolyl, tetrahydrobenzisothiazolyl, benzimidazolyl, tetrahydrobenzimidazolyl, benzodioxolyl, benzodithiolyl, benzodioxanyl, benzodithianyl, quinolinyl, isoquinolinyl, quinazolinyl, quinoxalinyl, phthalazinyl, naphthylidinyl or purinyl; or a bridged polycyclic heterocyclic group such as quinuclidinyl.

The secondary substituent of each of the alkyl group which may be substituted, the alkenyl group which may be substituted and the alkynyl group which may be substituted, may, for example, be halogen, hydroxyl, mercapto, alkoxy, alkylthio, alkenyloxy, alkenylthio, alkynyloxy, alkynylthio, cycloalkyl, cycloalkenyl, cycloalkoxy, cycloalkylthio, cycloalkenyloxy, cycloalkenylthio, alkoxycarbonyl, alkylcarbonyl, alkylcarbonyloxy, alkenyloxycarbonyl, alkenylcarbonyl, alkenylcarbonyloxy, alkynyloxycarbonyl, alkynylcarbonyl, alkynylcarbonyloxy, cycloalkoxycarbonyl, cycloalkylcarbonyl, cycloalkylcarbonyloxy, cycloalkenyloxycarbonyl, cycloalkenylcarbonyl, cycloalkenylcarbonyloxy, aryl, aryloxy, arylthio, aryloxycarbonyl, arylcarbonyl, arylcarbonyloxy, heterocyclyl, heterocyclyloxy, heterocyclylthio, heterocyclyloxycarbonyl, heterocyclylcarbonyl, heterocyclylcarbonyloxy, amino, cyano, nitro, carboxyl, aminocarbonyl, alkylsulfonyl, alkenylsulfonyl, alkynylsulfonyl, cycloalkylsulfonyl, cycloalkenylsulfonyl, arylsulfonyl, heterocyclylsulfonyl or aminosulfonyl. The number of such secondary substituents may be one or two or more, and such secondary substituents may be the same or different.

The secondary substituent of each of the cycloalkyl group which may be substituted, the cycloalkenyl group which may be substituted, the aryl group which may be substituted and the heterocyclic group which may be substituted, may, for example, be halogen, hydroxyl, mercapto, alkyl, alkenyl, alkynyl, alkoxy, alkylthio, alkenyloxy, alkenylthio, alkynyloxy, alkynylthio, cycloalkyl, cycloalkenyl, cycloalkoxy, cycloalkylthio, cycloalkenyloxy, cycloalkenylthio, alkoxycarbonyl, alkylcarbonyl, alkylcarbonyloxy, alkenyloxycarbonyl, alkenylcarbonyl, alkenylcarbonyloxy, alkynyloxycarbonyl, alkynylcarbonyl, alkynylcarbonyloxy, cycloalkoxycarbonyl, cycloalkylcarbonyl, cycloalkylcarbonyloxy, cycloalkenyloxycarbonyl, cycloalkenylcarbonyl, cycloalkenylcarbonyloxy, aryl, aryloxy, arylthio, aryloxycarbonyl, arylcarbonyl, arylcarbonyloxy, heterocyclyl, heterocyclyloxy, heterocyclylthio, heterocyclyloxycarbonyl, heterocyclylcarbonyl, heterocyclylcarbonyloxy, amino, cyano, nitro, carboxyl, aminocarbonyl, alkylsulfonyl, alkenylsulfonyl, alkynylsulfonyl, cycloalkylsulfonyl, cycloalkenylsulfonyl, arylsulfonyl, heterocyclylsulfonyl or aminosulfonyl. The number of such secondary substituents may be one or two or more, and such secondary substituents may be the same or different.

The secondary substituent of the amino group which may be substituted, which is included in the definition of the substituent in the formula (I), may, for example, be hydroxyl, alkyl, alkenyl, alkynyl, alkoxy, alkenyloxy, alkynyloxy, cycloalkyl, cycloalkenyl, cycloalkoxy, cycloalkenyloxy, alkoxycarbonyl, alkylcarbonyl, alkenyloxycarbonyl, alkenylcarbonyl, alkynyloxycarbonyl, alkynylcarbonyl, cycloalkoxycarbonyl, cycloalkylcarbonyl, cycloalkenyloxycarbonyl, cycloalkenylcarbonyl, aryl, aryloxy, aryloxycarbonyl, arylcarbonyl, heterocyclyl, heterocyclyloxy, heterocyclyloxycarbonyl, heterocyclylcarbonyl, aminocarbonyl, alkylsulfonyl, alkenylsulfonyl, alkynylsulfonyl, cycloalkylsulfonyl, cycloalkenylsulfonyl, arylsulfonyl, heterocyclylsulfonyl or aminosulfonyl. The number of such secondary substituents may be one or two or more, and such secondary substituents may be the same or different. Further, the two secondary substituents may form a ring containing or not containing a heteroatom.

Each of the substituent except halogen, hydroxyl, mercapto, cyano, nitro and carboxyl among the above secondary substituents may further be substituted with tertiary substituents such as halogen, hydroxyl, mercapto, cyano, nitro, carboxyl, amino, alkyl, alkenyl, alkynyl, cycloalkyl, cycloalkenyl, aryl, heterocyclyl, alkoxy, alkenyloxy, alkynyloxy, cycloalkyloxy, cycloalkenyloxy, aryloxy, heterocyclyloxy, alkylthio, alkenylthio, alkynylthio, cycloalkylthio, cycloalkenylthio, arylthio, heterocyclylthio, alkylsulfonyl, alkenylsulfonyl, alkynylsulfonyl, cycloalkylsulfonyl, cycloalkenylsulfonyl, arylsulfonyl, heterocyclylsulfonyl, alkylcarbonyl, alkenylcarbonyl, alkynylcarbonyl, cycloalkylcarbonyl, cycloalkenylcarbonyl, arylcarbonyl, heterocyclylcarbonyl, alkyloxycarbonyl, alkenyloxycarbonyl, alkynyloxycarbonyl, cycloalkyloxycarbonyl, cycloalkenyloxycarbonyl, aryloxycarbonyl, heterocyclyloxycarbonyl, aminocarbonyl, alkylaminocarbonyl, dialkylaminocarbonyl, alkenylaminocarbonyl, alkynylaminocarbonyl, cycloalkylaminocarbonyl, cycloalkenylaminocarbonyl, arylaminocarbonyl, heterocyclylaminocarbonyl, aminosulfonyl, alkylaminosulfonyl, dialkylaminosulfonyl, alkenylaminosulfonyl, alkynylaminosulfonyl, cycloalkylaminosulfonyl, cycloalkenylaminosulfonyl, arylaminosulfonyl, heterocyclylaminosulfonyl, alkylamino, dialkylamino, alkenylamino, alkynylamino, cycloalkylamino, cycloalkenylamino, arylamino, heterocyclylamino, alkylcarbonylamino, alkenylcarbonylamino, alkynylcarbonylamino, cycloalkylcarbonylamino, cycloalkenylcarbonylamino, arylcarbonylamino, heterocyclylcarbonylamino, alkylsulfonylamino, alkenylsulfonylamino, alkynylsulfonylamino, cycloalkylsulfonylamino, cycloalkenylsulfonylamino, arylsulfonylamino or heterocyclylsulfonylamino. The number of such tertiary substituents may be one or two or more, and when the number is two or more, such substituents may be the same or different. Further, when the secondary substituent is an amino group substituted with two tertiary substituents, such tertiary substituents together may form a ring containing or not containing a heteroatom.

The compounds of the formula (I) or salts thereof can have stereoisomers such as geometric isomers and optical isomers, and the present invention covers these isomers and mixtures thereof.

The compounds of the formula (I) and salts thereof can be produced by the following methods.

[Preparation Method 1]

A method comprising reacting a compound represented by the formula (II):

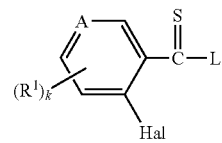

(wherein A, $R^1$, Hal and k are the same as defined above, and L is a leaving group) with a compound represented by the formula (III):

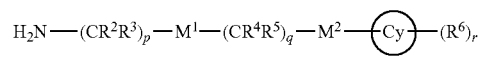

(wherein $M^1$, $M^2$, $R^2$, $R^3$, $R^4$, $R^5$, $R^6$, Cy, p, q and r are the same as defined above). The leaving group represented above as L may be a halogen atom, an alkoxy group or the like.

The reaction of the Preparation Method 1 may be carried out in the presence of a proper solvent. The specific solvent used may, for example, be an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethyl sulfoxide; a sulfone such as sulfolane; a phosphate amide such as hexamethylphosphoramide; or a halogenated hydrocarbon such as chloroform, dichloromethane, carbon tetrachloride or 1,2-dichloroethane, or a mixed solvent thereof.

In the Preparation Method 1, the reaction is carried out preferably in the presence of a base in some cases. The specific base used may, for example, be an organic base such as triethylamine, pyridine, N-methylmorpholine, 1,8-diazabicyclo[5.4.0]-7-undecene or N,N-dimethylaniline; an alkali metal such as lithium, sodium or potassium; an alkali metal carbonate such as lithium carbonate, sodium carbonate or potassium carbonate; an alkali metal hydrogencarbonate such as lithium hydrogencarbonate, sodium hydrogencarbonate or potassium hydrogencarbonate; an alkali metal hydride such as lithium hydride, sodium hydride or potassium hydride; or n-butyllithium, lithium diisopropylamide or sodium amide.

The reaction of the Preparation Method 1 is carried out usually at a reaction temperature of from −70 to 150° C., preferably at a reaction temperature of from −10 to 100° C. The reaction time is usually from 0.1 to 48 hours.

In the Preparation Method 1, the compound of the formula (III) may be used in an amount of from 0.8 to 2 equivalents, preferably from 1 to 1.5 equivalents, per 1 mol of the compound of the above formula (II).

In the Preparation Method 1, various reaction conditions may optionally be combined with one another. Further, such various reaction conditions include reaction conditions in a usual range and reaction conditions in a preferred range, and they may also be optionally selected and combined with one another.

[Preparation Method 2]

A method comprising reacting a compound represented by the formula (IV):

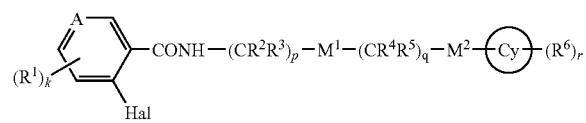

(wherein A, $R^1$, Hal, k, $M^1$, $M^2$, $R^2$, $R^3$, $R^4$, $R^5$, $R^6$, Cy, p, q and r are the same as defined above) with a thiocarbonylating agent.

The thiocarbonylating agent to be used in the reaction in the Preparation Method 2 is the Lawson reagent, diphosphorus pentasulfide or the like.

The reaction of the Preparation Method 2 may be carried out in the presence of a proper solvent. The specific solvent used may, for example, be an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; or carbon disulfide, or a mixed solvent thereof.

The reaction of the Preparation Method 2 is carried out usually at a reaction temperature of from −20 to 150° C., preferably at a reaction temperature of from 0 to 110° C. The reaction time is usually from 0.1 to 48 hours.

In the Preparation Method 2, the thiocarbonylating agent may be used in an amount of from 0.4 to 2 equivalents, per 1 mol of the compound of the above formula (IV).

In the Preparation Method 2, various reaction conditions may optionally be combined with one another. Further, such various reaction conditions include reaction conditions in a usual range and reaction conditions in a preferred range, and they may also be optionally selected and combined with one another.

The compound of the formula (IV) or a salt thereof can be produced by reacting a compound of the formula (V):

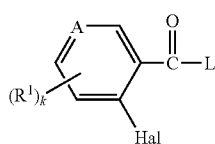

(wherein A, Hal, $R^1$, k and L are the same as defined above), instead of the compound of the formula (II), with the compound of the formula (III) the Preparation Method 1.

The compounds of the above formula (I) obtained by each of the above Preparation Methods 1 and 2 and methods in accordance therewith, may be isolated and purified by means of a known method such as concentration, concentration under reduced pressure, distillation, fractional distillation, redistribution, solvent extraction, crystallization, recrystallization or chromatography. In a case where the compound of the above formula (I) is obtained as a free form, a salt may be formed by a conventional method.

Further, the compound of the above formula (I) or a salt thereof or a stereoisomer thereof has a cytokine production inhibitory effect by itself or as mixed.

EFFECTS OF THE INVENTION

The present invention provides a cytokine production inhibitor useful as a preventive or therapeutic medicine for diseases accompanied by hyperactivated immune functions.

BEST MODE FOR CARRYING OUT THE INVENTION

The preferable embodiments of the compounds of the above formula (I) or salts thereof are described below.

(1) Compounds of the above formula (I) or salts thereof wherein A is a nitrogen atom, C—$NO_2$ or C—CN; Hal is a halogen atom; $M^1$ is an alkyl group which may be substituted, an alkenyl group which may be substituted, an alkynyl group which may be substituted, a cycloalkyl group which may be substituted or an aryl group which may be substituted; $R^1$ is a halogen atom or a nitro group; each of $R^2$, $R^3$, $R^4$ and $R^5$ is independently a hydrogen atom or an alkyl group which may be substituted; $R^6$ is a halogen atom, an alkyl group which may be substituted, a heterocyclic group which may be substituted, an amino group which may be substituted or B-Q (wherein B is an oxygen atom or a sulfur atom; and Q is a hydrogen atom, an alkyl group which may be substituted or a cycloalkyl group which may be substituted); and Cy is a cycloalkyl group, an aryl group or a heterocyclic group.

(2) Compounds of the above formula (I) or salts thereof wherein p and q are 0.

(3) Compounds of the above formula (I) or salts thereof wherein A is C—$NO_2$.

(4) The compounds according to (1) or salts thereof wherein A is C—$NO_2$.

(5) The compounds according to (4) or salts thereof wherein $M^1$ is an alkyl group which may be substituted or an aryl group which may be substituted.

(6) The compounds according to (4) or salts thereof wherein $M^2$ is an amino group which may be substituted, an oxygen atom or a sulfur atom.

(7) The compounds according to (4) or salts thereof wherein Cy is a heterocyclic group.

Other preferred specific examples of the compounds are listed below in Table 1.

TABLE 1

| A | Hal | (R¹)ₖ | (CR²R³)ₚ | —M¹— | (CR⁴R⁵)_q | M² | Cy | (R⁶)_r |
|---|---|---|---|---|---|---|---|---|
| C—NO₂ | Cl | k = 0 | p = 0 | *para*-phenylene | q = 0 | O | 2-Pyridyl | 3-Cl, 5-CF₃ |
| C—NO₂ | Cl | k = 0 | p = 0 | *para*-phenylene | q = 0 | O | 2-Pyridyl | 6-Cl, 4-CF₃ |
| C—NO₂ | Cl | k = 0 | p = 0 | —(CH₂)₃— | q = 0 | O | 2-Pyridyl | 6-Piperidino, 4-CF₃ |
| C—NO₂ | Cl | k = 0 | p = 0 | —(CH₂)₃— | q = 0 | O | 2-Pyridyl | 6-Thiomorpholino, 4-CF₃ |
| C—NO₂ | Cl | k = 0 | p = 0 | *para*-phenylene | q = 0 | S | 2-Pyridyl | 3-Cl, 5-CF₃ |
| C—NO₂ | Cl | k = 0 | p = 0 | *para*-phenylene | q = 0 | NH | 2-Pyridyl | 3-Cl, 5-CF₃ |
| C—NO₂ | Cl | k = 0 | p = 0 | *para*-phenylene | q = 0 | S | 2-Pyridyl | 6-Cl, 4-CF₃ |
| C—NO₂ | Cl | k = 0 | p = 0 | —(CH₂)₃— | q = 0 | O | 2-Pyridyl | 4-CF₃, 6-Dimethylamino |
| C—NO₂ | F | k = 0 | p = 0 | *para*-phenylene | q = 0 | O | 2-Pyridyl | 3-Cl, 5-CF₃ |
| C—NO₂ | Cl | k = 0 | p = 0 | —(CH₂)₃— | q = 0 | O | 2-Pyridyl | 6-(2-Propyloxy), 4-CF₃ |
| C—NO₂ | Cl | k = 0 | p = 0 | 2-F-phenylene | q = 0 | O | 2-Pyridyl | 3-Cl, 5-CF₃ |
| C—NO₂ | F | k = 0 | p = 0 | 3-F-phenylene | q = 0 | O | 2-Pyridyl | 3-Cl, 5-CF₃ |
| C—NO₂ | F | 3-F, 4-F | p = 0 | *para*-phenylene | q = 0 | O | 2-Pyridyl | 3-Cl, 5-CF₃ |
| C—NO₂ | F | 4-NO₂ | p = 0 | *para*-phenylene | q = 0 | O | 2-Pyridyl | 3-Cl, 5-CF₃ |
| C—NO₂ | Cl | k = 0 | p = 0 | —(CH₂)₃— | q = 0 | O | Pyrimidin-2-yl | 4-Methoxy, 6-Methoxy |

TABLE 1-continued

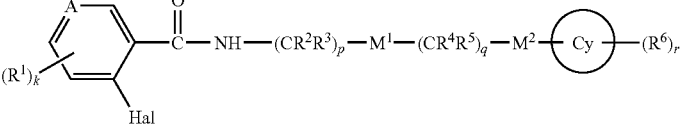

| A | Hal | (R¹)$_K$ | (CR²R³)$_P$ | —M¹— | (CR⁴R⁵)$_q$ | M² | Cy | (R⁶)$_r$ |
|---|---|---|---|---|---|---|---|---|
| C—NO₂ | Cl | k = 0 | p = 0 |  | q = 0 | O | Pyrimidin-2-yl | 4-Methoxy, 6-Methoxy |
| N | Cl | 6-Cl | p = 0 | 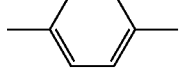 | q = 0 | O | 2-Pyridyl | 3-Cl, 5-CF₃ |
| C—NO₂ | F | k = 0 | p = 0 | —(CH₂)₃— | q = 0 | O | 2-Pyridyl | 6-Dimethylamino, 4-CF₃ |
| N | Cl | 6-Cl | p = 0 | 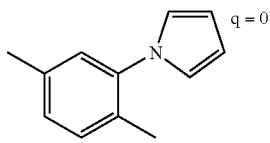 | q = 0 | O | 2-Pyridyl | 3-Cl, 5-CF₃ |
| C—CN | Cl | k = 0 | p = 0 | 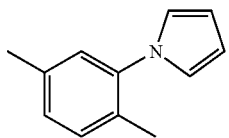 | q = 0 | O | 2-Pyridyl | 3-Cl, 5-CF₃ |
| C—NO₂ | Cl | k = 0 | p = 0 |  | q = 0 | O | 2-Pyridyl | 3-Cl, 5-CF₃ |
| C—NO₂ | Cl | k = 0 | p = 0 |  | q = 0 | O | 2-Pyridyl | 6-Cl, 4-CF₃ |
| C—NO₂ | Cl | k = 0 | CH₂ |  | q = 0 | O | 2-Pyridyl | 3-Cl, 5-CF₃ |
| C—NO₂ | Cl | k = 0 | CH₂ | 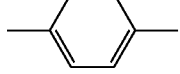 | q = 0 | O | 2-Pyridyl | 6-Cl, 4-CF₃ |
| C—NO₂ | Cl | k = 0 | p = 0 | —(CH₂)₃— | q = 0 | O | 2-Pyridyl | 3-Cl, 5-CF₃ |
| C—NO₂ | Cl | k = 0 | p = 0 | —(CH₂)₃— | q = 0 | S | 2-Pyridyl | 3-Cl, 5-CF₃ |
| C—NO₂ | Cl | k = 0 | p = 0 | —(CH₂)₃— | q = 0 | NH | 2-Pyridyl | 3-Cl, 5-CF₃ |
| C—NO₂ | F | k = 0 | p = 0 | —(CH₂)₃— | q = 0 | NH | 2-Pyridyl | 3-Cl, 5-CF₃ |
| C—NO₂ | Cl | k = 0 | p = 0 | —(CH₂)₃— | q = 0 | O | 2-Pyridyl | 6-Cl, 4-CF₃ |
| C—NO₂ | Cl | k = 0 | CH₂ |  | CH₂ | O | 2-Pyridyl | 3-Cl, 5-CF₃ |
| C—NO₂ | Cl | k = 0 | CH₂ |  | CH₂ | O | 2-Pyridyl | 6-Cl, 4-CF₃ |
| C—NO₂ | Cl | k = 0 | CH₂ |  | CH₂ | O | 2-Pyridyl | 3-Cl, 5-CF₃ |
| C—NO₂ | F | k = 0 | CH₂ |  | CH₂ | O | 2-Pyridyl | 6-Cl, 4-CF₃ |

TABLE 1-continued

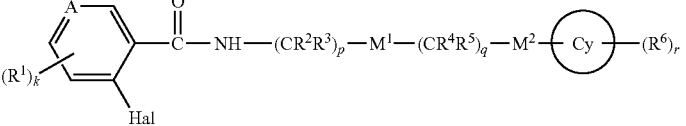

| A | Hal | $(R^1)_K$ | $(CR^2R^3)_P$ | —M¹— | $(CR^4R^5)_q$ | M² | Cy | $(R^6)_r$ |
|---|---|---|---|---|---|---|---|---|
| C—NO₂ | F | k = 0 | CH₂ | cis-CH=CH | CH₂ | O | 2-Pyridyl | 3-Cl, 5-CF₃ |
| C—NO₂ | Cl | k = 0 | CH₂ | cis-CH=CH | CH₂ | O | 2-Pyridyl | 3-Cl, 5-CF₃ |
| C—NO₂ | Cl | k = 0 | CH₂ | —C≡C— | CH₂ | O | 2-Pyridyl | 3-Cl, 5-CF₃ |
| C—NO₂ | F | k = 0 | CH₂ | —C≡C— | CH₂ | O | 2-Pyridyl | 3-Cl, 5-CF₃ |
| C—NO₂ | Cl | k = 0 | CH₂ | 1,4-cyclohexylene | q = 0 | O | 2-Pyridyl | 3-Cl, 5-CF₃ |
| C—NO₂ | Cl | k = 0 | CH₂ | 1,4-cyclohexylene | q = 0 | O | 2-Pyridyl | 6-Cl, 4-CF₃ |
| C—NO₂ | Cl | k = 0 | p = 0 | —(CH₂)₂— | q = 0 | O | 2-Pyridyl | 3-Cl, 5-CF₃ |
| C—NO₂ | Cl | k = 0 | p = 0 | —(CH₂)₂— | q = 0 | O | 2-Pyridyl | 6-Cl, 4-CF₃ |
| C—NO₂ | Cl | k = 0 | p = 0 | —(CH₂)₂— | q = 0 | S | 2-Pyridyl | 6-Cl, 4-CF₃ |
| C—NO₂ | F | k = 0 | CH₂ | —C(CH₃)₂— | CH₂ | O | 2-Pyridyl | 3-Cl, 5-CF₃ |
| C—NO₂ | F | k = 0 | p = 0 | —(CH₂)₃— | q = 0 | O | 2-Pyridyl | 6-Ethoxy, 4-CF₃ |
| N | Cl | k = 0 | p = 0 | 2,4-dimethylphenylene | q = 0 | Single bond | 1-Adamantyl | r = 0 |
| C—NO₂ | F | k = 0 | p = 0 | —(CH₂)₃— | q = 0 | O | 2-Pyridyl | 6-Methoxy, 4-CF₃ |
| C—NO₂ | Cl | k = 0 | p = 0 | —(CH₂)₃— | q = 0 | O | 2-Pyridyl | 6-Pyrrolidinyl, 4-CF₃ |
| C—NO₂ | F | k = 0 | p = 0 | —(CH₂)₃— | q = 0 | O | 2-Pyridyl | 6-Pyrrolidinyl, 4-CF₃ |
| C—NO₂ | Cl | k = 0 | p = 0 | —(CH₂)₃— | q = 0 | O | 2-Pyridyl | 6-(1H-Pyrrol-1-yl), 4-CF₃ |
| C—NO₂ | F | k = 0 | p = 0 | —(CH₂)₃— | q = 0 | O | 2-Pyridyl | 6-(1H-Pyrrol-1-yl), 4-CF₃ |
| C—NO₂ | F | k = 0 | p = 0 | —(CH₂)₃— | q = 0 | O | 2-Pyridyl | 3-(1H-Pyrrol-1-yl), 5-CF₃ |
| C—NO₂ | Cl | k = 0 | p = 0 | —(CH₂)₃— | q = 0 | O | 2-Pyridyl | 3-(1H-Pyrrol-1-yl), 5-CF₃ |
| C—NO₂ | Cl | k = 0 | p = 0 | —(CH₂)₃— | q = 0 | NH | 2-Pyridyl | 3-Cl, 5-CF₃, 6-Cl |
| C—NO₂ | F | k = 0 | p = 0 | —(CH₂)₃— | q = 0 | NH | 2-Pyridyl | 3-Cl, 5-CF₃, 6-Cl |
| C—NO₂ | Cl | k = 0 | p = 0 | —(CH₂)₃— | q = 0 | NH | 2-Pyridyl | 6-CF₃ |
| C—NO₂ | F | k = 0 | p = 0 | —(CH₂)₃— | q = 0 | NH | 2-Pyridyl | 5-Cl, 3-CF₃ |
| C—NO₂ | F | k = 0 | p = 0 | —(CH₂)₃— | q = 0 | O | Phenyl | 3-CF₃, 5-CF₃ |
| C—NO₂ | Cl | k = 0 | p = 0 | —(CH₂)₃— | q = 0 | O | Phenyl | 3-CF₃, 5-CF₃ |
| C—NO₂ | Cl | k = 0 | p = 0 | —(CH₂)₃— | q = 0 | O | 2-Pyridyl | 4-CF₃, 5-CF₃ |
| C—NO₂ | F | k = 0 | p = 0 | —(CH₂)₃— | q = 0 | O | 2-Pyridyl | 4-CF₃, 5-CF₃ |
| N | Cl | 6-Cl | p = 0 | 1,4-phenylene | q = 0 | NH | 2-Pyridyl | 3-Cl, 5-CF₃ |

TABLE 1-continued

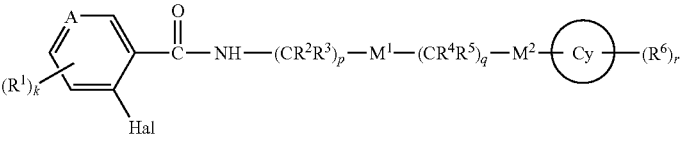

| A | Hal | $(R^1)_K$ | $(CR^2R^3)_P$ | —M¹— | $(CR^4R^5)_q$ | M² | Cy | $(R^6)_r$ |
|---|---|---|---|---|---|---|---|---|
| N | F | 6-Cl | p = 0 | 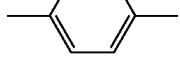 | q = 0 | NH | 2-Pyridyl | 3-Cl, 5-CF₃ |
| C—NO₂ | Cl | k = 0 | p = 0 | —(CH₂)₃— | q = 0 | O | 2-Pyridyl | 3-Cl, 5-Cl |
| C—NO₂ | F | k = 0 | p = 0 | —(CH₂)₃— | q = 0 | O | 2-Pyridyl | 3-Cl, 5-Cl |
| C—NO₂ | Cl | k = 0 | p = 0 |  | q = 0 | NH | 2-Pyridyl | 3-Cl, 5-CF₃ |
| C—NO₂ | F | k = 0 | p = 0 | 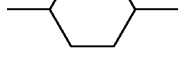 | q = 0 | NH | 2-Pyridyl | 3-Cl, 5-CF₃ |
| C—NO₂ | F | k = 0 | p = 0 | —(CH₂)₃— | q = 0 | O | Phenyl | 3-CF₃ |
| C—NO₂ | Cl | k = 0 | p = 0 | —(CH₂)₃— | q = 0 | O | Phenyl | 3-CF₃ |
| C—NO₂ | Cl | k = 0 | p = 0 | 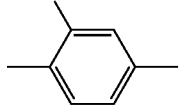 | q = 0 | NH | 2-Pyridyl | 3-Cl, 5-CF₃ |
| C—NO₂ | F | k = 0 | p = 0 | 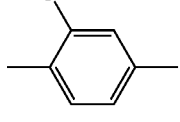 | q = 0 | NH | 2-Pyridyl | 3-Cl, 5-CF₃ |
| N | Cl | 6-Cl | p = 0 | 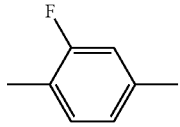 | q = 0 | O | 2-Pyridyl | 3-Cl, 5-CF₃ |
| N | Cl | 6-Cl | p = 0 | 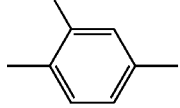 | q = 0 | O | 2-Pyridyl | 6-Cl, 4-CF₃ |
| C—NO₂ | F | k = 0 | CH₂ | 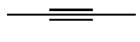 | CH₂ | O | 2-Pyridyl | 3-Dimethylamino, 5-CF₃ |
| C—NO₂ | F | k = 0 | p = 0 | 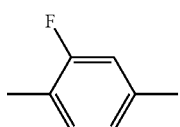 | q = 0 | S | 2-Pyridyl | 3-Cl, 5-CF₃ |
| C—NO₂ | Cl | k = 0 | p = 0 | 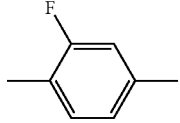 | q = 0 | S | 2-Pyridyl | 3-Cl, 5-CF₃ |

TABLE 1-continued

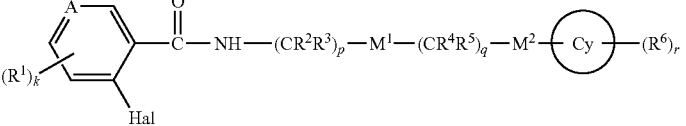

| A | Hal | $(R^1)_K$ | $(CR^2R^3)_P$ | —M¹— | $(CR^4R^5)_q$ | M² | Cy | $(R^6)_r$ |
|---|---|---|---|---|---|---|---|---|
| C—NO$_2$ | F | k = 0 | p = 0 | 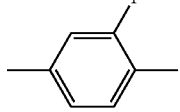 | q = 0 | O | 2-Pyridyl | 3-Cl, 5-CF$_3$ |
| C—NO$_2$ | Cl | k = 0 | p = 0 | 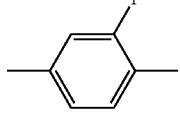 | q = 0 | O | 2-Pyridyl | 3-Cl, 5-CF$_3$ |
| C—NO$_2$ | Cl | k = 0 | CH$_2$ | 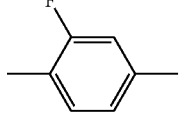 | q = 0 | O | 2-Pyridyl | 3-Cl, 5-CF$_3$ |
| C—NO$_2$ | Cl | k = 0 | CH$_2$ | 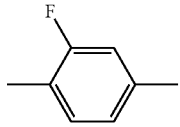 | q = 0 | O | 2-Pyridyl | 3-Cl, 5-CF$_3$ |
| N | Cl | 6-Cl | p = 0 | 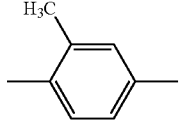 | q = 0 | O | 2-Pyridyl | 3-Cl, 5-CF$_3$ |
| C—NO$_2$ | F | k = 0 | CH$_2$CH$_2$ | O | CH$_2$ | Single bond | Phenyl | 3-CF$_3$, 5-CF$_3$ |
| C—NO$_2$ | F | k = 0 | CH$_2$CH$_2$ | O | CH$_2$ | Single bond | Phenyl | 3-CF$_3$, 5-CF$_3$ |
| C—NO$_2$ | Cl | k = 0 | p = 0 | —(CH$_2$)$_3$— | q = 0 | NH | 2-Pyridyl | 3-Piperidino, 5-CF$_3$ |
| C—NO$_2$ | F | k = 0 | p = 0 | —(CH$_2$)$_3$— | q = 0 | NH | 2-Pyridyl | 3-Piperidino, 5-CF$_3$ |
| C—NO$_2$ | Cl | k = 0 | p = 0 | CH$_2$ | q = 0 | Single bond | Phenyl | 4-CF$_3$ |
| C—NO$_2$ | F | k = 0 | p = 0 | CH$_2$ | q = 0 | Single bond | Phenyl | 4-CF$_3$ |
| C—NO$_2$ | Cl | k = 0 | p = 0 | —(CH$_2$)$_3$— | q = 0 | O | 2-Pyridyl | 6-Methylthio, 4-CF$_3$ |
| C—NO$_2$ | F | k = 0 | p = 0 | —(CH$_2$)$_3$— | q = 0 | O | 2-Pyridyl | 6-Methylthio, 4-CF$_3$ |
| C—NO$_2$ | F | k = 0 | p = 0 | —(CH$_2$)$_4$— | q = 0 | S | 2-Pyridyl | 6-Dimethylamino, 4-CF$_3$ |
| C—NO$_2$ | F | k = 0 | p = 0 | —(CH$_2$)$_3$— | q = 0 | O | 2-Pyridyl | 6-Cyclopentyloxy, 4-CF$_3$ |
| C—NO$_2$ | F | k = 0 | p = 0 | 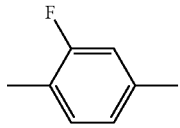 | q = 0 | O | 2-Pyrimidinyl | 4-Methoxy, 6-Methoxy |
| C—NO$_2$ | F | k = 0 | CH$_2$ |  | CH$_2$ | O | 2-Pyridyl | 3-Dimethylamino, 5-CF$_3$ |

The compounds represented by the above formula (VI):

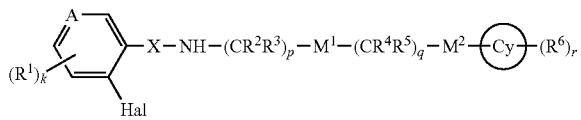

(wherein X is SO₂ or CO; A is a nitrogen atom, N-oxide, C—NO₂ or C—CN; Hal is a halogen atom; M¹ is an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted, an oxygen atom, a sulfur atom, SO or SO₂; M² is an amino group which may be substituted, an oxygen atom, a sulfur atom or a single bond; R¹ is a halogen atom, a cyano group, a nitro group, an alkyl group which may be substituted, an alkoxy group which may be substituted, an alkylthio group which may be substituted, an amino group which may be substituted or a heterocyclic group which may be substituted; each of R², R³, R⁴ and R⁵ is independently a hydrogen atom, an alkyl group which may be substituted, a cyano group or an alkyloxycarbonyl group; R⁶ is a halogen atom, a cyano group, a nitro group, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted or B-Q (wherein B is a carbonyl group, a carbonyloxy group, an oxycarbonyl group, an oxygen atom, a sulfur atom, SO or SO₂; and Q is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted or an amino group which may be substituted); Cy is a cycloalkyl group, a cycloalkenyl group, an aryl group or a heterocyclic group; each of k, p and q is independently an integer of from 0 to 3; and r is an integer of from 0 to 5; provided that (1) when A is C—NO₂ or C—CN, and p is 0, M¹ is an alkyl group which may be substituted, an alkenyl group which may be substituted, an alkynyl group which may be substituted, a cycloalkyl group which may be substituted, a cycloalkenyl group which may be substituted, an amino group which may be substituted, an oxygen atom, a sulfur atom, SO or SO₂, and (2) N-(1-adamantyl)methyl-2-chloro-5-nitrobenzamide is excluded] or salts thereof also have cytokine production inhibitory effects like the compounds of the above formula (I) or salts thereof. Preferred embodiments of the compounds are described below.

(1) Compounds of the formula (VI) or salts thereof wherein X is SO₂; A is C—NO₂; Hal is a halogen atom; M¹ is an alkyl group which may be substituted, an alkenyl group which may be substituted, an alkynyl group which may be substituted, a cycloalkyl group which may be substituted, a cycloalkenyl group which may be substituted, an amino group which may be substituted, an oxygen atom, a sulfur atom, SO or SO₂; R¹ is a halogen atom, a cyano group, a nitro group, an alkyl group which may be substituted, an alkoxy group which may be substituted, an alkylthio group which may be substituted, an amino group which may be substituted or a heterocyclic group which may be substituted; Cy is a cycloalkyl group, a cycloalkenyl group, an aryl group or a heterocyclic group; and k is an integer of from 0 to 3 (provided that when Hal is a chlorine atom, (R¹)ₖ is not a chlorine atom at the ortho position to X or a nitro group at the meta position to X).

(2) The compounds according to (1) or salts thereof wherein M¹ is an alkyl group, and k is 0 (provided that 2-chloro-5-nitro-N-(2-phenoxyethyl)benzenesulfonamide is excluded).

(3) The compounds according to (1) or salts thereof wherein M¹ is an alkyl group, Cy is a cycloalkyl group, a cycloalkenyl group, an aryl group or a heterocyclic group (except for an indolyl group, an adamantyl group, a 3-pyridyl group, a 4-pyridyl group, a tetrahydro-2-furanyl group, a 2-furanyl group and a 1,3-benzodioxolyl-5-yl group), and k is 0.

(4) Compounds of the formula (VI) or salts thereof wherein X is SO₂, and A is C—CN (provided that N-(2-furanylmethyl)-4-amino-2-chloro-5-cyanobenzenesulfonamide is excluded).

(5) Compounds of the formula (VI) or salts thereof wherein X is SO₂, and A is a nitrogen atom (provided that 4-chloro-N-[(1-ethyl-2-pyrrolidinyl)methyl]-3-pyridinesulfonamide is excluded).

(6) Compounds of the formula (VI) or salts thereof wherein X is CO, A is C—NO₂, M¹ is an alkyl group which may be substituted, an alkenyl group which may be substituted, an alkynyl group which may be substituted or a cycloalkyl group which may be substituted, Cy is a cycloalkyl group, an aryl group or a heterocyclic group, and p and q are 0.

(7) The compounds according to (6) or salts thereof wherein Cy is a phenyl group or a 6-membered monocyclic heterocyclic group.

(8) Compounds of the formula (VI) or salts thereof wherein X is CO, A is a nitrogen atom, and p and q are 0.

(9) Compounds of the formula (VI) or salts thereof wherein X is CO, A is a nitrogen atom, M¹ is an alkyl group which may be substituted, an aryl group which may be substituted or a heterocyclic group which may be substituted, M² is an amino group which may be substituted, an oxygen atom or a single bond, Cy is a cycloalkyl group or a heterocyclic group, and p and q are 0.

(10) The compounds according to (9) or salts thereof wherein Cy is an adamantyl group or a 6-membered monocyclic heterocyclic group.

(11) The compounds according to (9) or salts thereof wherein Cy is a 6-membered monocyclic heterocyclic group.

The compounds of the above formulae (I) and (VI) or salts thereof are compounds which exhibit cytokine production inhibitory activity, and are useful as preventive or therapeutic medicines for diseases accompanied by hyperactivated immune functions as listed below.

(1) At least one type of allergic diseases selected from urticaria, food allergy, anaphylactic shock, hypereosinophilic syndrome, asthma, allergic rhinitis, allergic conjunctivitis and atopic dermatitis.

(2) Systemic autoimmune diseases in which antibody production or humoral immunity is hyperactivated.

(3) At least one type of organ specific autoimmune diseases selected from chronic rheumatoid arthritis, type I diabetes, Hashimoto's thyroiditis, myasthenia gravis and multiple sclerosis.

(4) Graft rejection accompanying organ transplantation.

The compounds of the formula (I) are usually used in the form of a common pharmaceutical preparation (such as a method as defined in the Japanese Pharmacopoeia Twelfth Edition). The pharmaceutical preparation is prepared by using a commonly used diluent or excipient such as a bulking agent, an extender, a binding agent, a moisture-imparting agent, a disintegrator, a surfactant or a lubricant. As the pharmaceutical preparation, various forms may be selected depending upon the purpose of treatment, and a tablet, a pill, a powder, a dust, a granule, a capsule, a suppository, a solution, a suspension, an emulsion, an injection (such as a solution or a suspension), a spray, an aerosol, a cream, an ointment, a lotion or a transdermal agent (a patch, a matrix or a tape) may be mentioned as examples.

To form the medicine into a tablet, carriers which have conventionally been known in this field can be used widely, and they may, for example, be excipients such as lactose, sucrose, sodium chloride, glucose, urea, starch, calcium carbonate, kaolin, crystalline cellulose and silicic acid; binding agents such as water, ethanol, propanol, simple syrup, a glucose solution, a starch solution, a gelatin solution, carboxymethyl cellulose, Shellac, methyl cellulose, potassium phosphate and polyvinyl pyrrolidone; disintegrators such as dried starch, sodium alginate, an agar powder, a laminaran powder, sodium hydrogencarbonate, calcium carbonate, polyoxyethylene sorbitan fatty acid esters, sodium lauryl sulfate, monoglyceryl stearate, starch and lactose; disintegration inhibitors such as sucrose, stearin, cacao butter and hydrogenated oil; absorption enhancers such as a quaternary ammonium base and sodium lauryl sulfate, humectants such as glycerin and starch, adsorbents such as starch, lactose, kaolin, bentonite and colloidal silicate, and lubricants such as purified talc, a stearate, a boric acid powder and polyethylene glycol. Further, a tablet may be a tablet having a common coating applied thereto as the case requires, such as a sugar-coated tablet, a gelatin-coated tablet, an enteric-coated tablet or a film-coated tablet, or a double tablet or a multilayer tablet.

To form the medicine into a pill, carriers which have conventionally been known in this field can be used widely, and they may, for example, be excipients such as glucose, lactose, starch, cacao butter, hydrogenated vegetable oil, kaolin and talc; binding agents such as powdered acacia, powdered tragacanth, gelatin and ethanol and disintegrators such as laminaran agar.

To form the medicine into a suppository, conventionally known carriers can be used widely, and they may, for example, be polyethylene glycol, cacao butter, higher alcohols, higher alcohol esters, gelatin and semi-synthetic glyceride.

To prepare an injection, a solution, an emulsion or a suspension is sterilized, and is preferably isotonic with the blood, and to form the medicine into a solution, an emulsion or a suspension, all the diluents which are commonly used in this field can be used, and they may, for example, be water, a lactic acid aqueous solution, ethyl alcohol, propylene glycol, ethoxylated isostearyl alcohol, polyoxylated isostearyl alcohol and polyoxyethylene sorbitan fatty acid esters. In this case, sodium chloride salt, glucose or glycerin in an amount adequate to prepare an isotonic solution may be incorporated in the pharmaceutical preparation, and a common solubilizing agent, buffer, soothing agent or the like may be added thereto. Further, as the case requires, a colorant, a preservative, a fragrant material, a flavoring agent, a sweetening agent or another pharmaceutical agent may be incorporated in the pharmaceutical preparation.

The amount of the compound of the formula (I) is not particularly limited and may optionally be selected from a wide range, but it is usually from 1 to 70 wt %, preferably from 5 to 50 wt % in the entire composition.

The administration method of the compounds of the formula (I) is not particularly limited, and they are orally or parenterally administered by a method depending upon the form of the preparation, the age, the sex or other conditions of the patient and the degree of the disease. For example, for oral administration, a tablet, a pill, a solution, a suspension, an emulsion, a granule or a capsule may, for example, be mentioned as a preferred form. For parenteral administration, the medicine may be administered in the form of e.g. a topical agent, an injection, a transdermal agent, nasal drops, an inhalant or a suppository. In the case of an injection, it is preferred that the medicine is intravenously administered by itself or as mixed with a conventional fluid replacement such as glucose or amino acids, or as the case requires, it is intramuscularly, intracutaneously, subcutaneously or intraperitoneally administered by itself. Further, in the case of a suppository, it is preferred that the medicine is administered in rectum.

The dose of the compound of the formula (I) is optionally selected depending upon e.g. the direction for use, the age, the sex or other conditions of the patient and the degree of disease, and usually the amount of the compound of the above formula (I) as an active ingredient is preferably from about 0.05 to about 50 mg per kg of the body weight per day, and the medicine may be administered once or several times a day. Further, it is preferred that the active ingredient is contained in an amount of from 1 to 1,000 mg in the administration unit form.

EXAMPLES

Now, Examples (Preparation Examples and Test Examples) of the present invention will be described, however, the present invention is by no means restricted thereto.

Preparation Example 1

Preparation of N-(4-(3-chloro-5-trifluoromethyl-2-pyridyloxy)phenyl)-2-chloro-5-nitrothiobenzamide (Compound No. 1)

A solution of 410 mg of N-(4-(3-chloro-5-trifluoromethyl-2-pyridyloxy)phenyl)-2-chloro-5-nitrobenzamide and 452 mg of the Lawson reagent in 10 mL toluene was stirred overnight under heating with reflux. After completion of the reaction, the solution was allowed to cool, and the solvent was evaporated under reduced pressure. Ethyl acetate was added to the residue, and the insolubles were filtered away. The filtrate was concentrated under reduced pressure, and the resulting crude product was purified by column chromatography to give 312 mg of N-(4-(3-chloro-5-trifluoromethyl-2-pyridyloxy)phenyl)-2-chloro-5-nitrothiobenzamide (Compound No. 1) having a melting point of 186-187° C.

The following compounds can be produced in the same manner as in Preparation Example 1.

Compound No. 2: N-(4-(6-chloro-4-trifluoromethyl-2-pyridyloxy)phenyl)-2-chloro-5-nitrothiobenzamide (m.p. 186-187° C.)

Compound No. 3: N-(3-(6-piperidino-4-trifluoromethyl-2-pyridyloxy)propyl)-2-chloro-5-nitrothiobenzamide (oil)

Compound No. 4: N-(3-(6-thiomorpholino-4-trifluoromethyl-2-pyridyloxy)propyl)-2-chloro-5-nitrothiobenzamide (m.p. 132-133° C.)

Compound No. 5: N-(4-(3-chloro-5-trifluoromethyl-2-pyridylthio)phenyl)-2-chloro-5-nitrothiobenzamide (m.p. 72-73° C.)

Compound No. 6: N-(4-(3-chloro-5-trifluoromethyl-2-pyridylamino)phenyl)-2-chloro-5-nitrothiobenzamide (m.p. 199-200° C.)

Compound No. 7: N-(4-(6-chloro-4-trifluoromethyl-2-pyridylthio)phenyl)-2-chloro-5-nitrothiobenzamide (m.p. 183-186° C.)

Compound No. 8: N-(3-(6-dimethylamino-4-trifluoromethyl-2-pyridyloxy)propyl)-2-chloro-5-nitrothiobenzamide (m.p. 102-103° C.)

Compound No. 9: N-(4-(3-chloro-5-trifluoromethy-2-pyridyloxy)phenyl)-2-fluoro-5-nitrothiobenzamide (m.p. 167-168° C.)

Compound No. 10: N-(3-(6-isopropoxy-4-trifluoromethyl-2-pyridyloxy)propyl)-2-chloro-5-nitrothiobenzamide (oil)

Compound No. 11: N-(4-(3-chloro-5-trifluoromethyl-2-pyridyloxy)-2-fluorophenyl)-2-chloro-5-nitrothiobenzamide (m.p. 193° C.)

Compound No. 12: N-(4-(3-chloro-5-trifluoromethyl-2-pyridyloxy)-2-fluorophenyl)-2-fluoro-5-nitrothiobenzamide (m.p. 146-147° C.)

Compound No. 13: N-(4-(3-chloro-5-trifluoromethyl-2-pyridyloxy)phenyl)-4,6-dichlorothionicotinamide (m.p. 175-176° C.)

Compound No. 14: N-(4-(3-chloro-5-trifluoromethyl-2-pyridyloxyphenyl)-2,3,4-trifluoro-5-nitrothibenzamide (m.p. 124-126° C.)

Compound No. 15: N-(4-(3-chloro-5-trifluoromethyl-2-pyridyloxyphenyl)-2-fluoro-4,5-dinitrobenzamide (m.p. 167-169° C.)

Compound No. 16: N-(3-(6-dimethylamino-4-trifluoromethyl-2-pyridyloxy)propyl)-2-fluoro-5-nitrothiobenzamide (m.p. 130-133° C.)

Compound No. 17: N-(4-(3-chloro-5-trifluoromethyl-2-pyridyloxy)-3-(1H-pyrrol-1-yl)phenyl)-2-chloro-5-cyanothiobenzamide (m.p. 229-230° C.)

Compound No. 18: N-(3-(4,6-dimethoxy-2-pyrimidinyloxy)propyl)-2-chloro-5-nitrothiobenzamide (m.p. 119-120° C.)

Compound No. 19: N-(4-(4,6-dimethoxy-2-pyrimidinyloxy)phenyl)-2-chloro-5-nitrothiobenzamide (m.p. 220-222° C.)

Reference Preparation Example 1

Preparation of N-(2-(3-chloro-5-trifluoromethyl-2-pyridyloxy)ethyl)-2-chloro-5-nitrobenzamide A solution of 600 mg of N-(2-(3-chloro-5-trifluoromethyl-2-pyridyloxy)ethylphthalimide and 85 mg of hydrazine monohydrate in 8 mL of methanol was stirred at about 55-60° C. for about 6 hours. The solution was allowed to cool and then stirred with 16 mL of ether. The insolubles were filtered away, and the filtrate was concentrated under reduced pressure. The concentrate was dissolved in 6 mL of acetonitrile, and, after successive addition of 190 mg of triethylamine and 350 mg of 2-chloro-5-nitrobenzoyl chloride, stirred for about 1 hour. After the reaction, water was added, and the reaction solution was extracted with ethyl acetate. The extract was dried over with sodium sulfate and concentrated under reduced pressure to give a crude product. The crude product was purified by column chromatography to give 350 mg of N-(2-(3-chloro-5-trifluoromethyl-2-pyridyloxy)ethyl)-2-chloro-5-nitrobenzamide having a melting point of 126-127° C.

Reference Preparation Example 2

Preparation of N-(4-(3-chloro-5-trifluoromethyl-2-pyridyloxy)phenyl)-4-chloronicotinamide A solution of 150 mg of 4-(3-chloro-5-trifluoromethyl-2-pyridyloxy)aniline and 116 mg of triethylamine in 5 mL of tetrahydrofuran was stirred with 100 mg of 4-chloronicotinoyl chloride hydrochloride for about 50 minutes, and after addition of water, the precipitated crystals were recovered by filtration. The recovered crystals were washed with ether and dried to 106 mg of N-(4-(3-chloro-5-trifluoromethyl-2-pyridyloxy)phenyl)-4-chloronicotinamide having a melting point of 178-180° C. (decomposition).

Specific examples of the compounds of the above formula (VI), which can be produced in accordance with Reference Examples 1 and 2 and the Preparation Method 1, are shown below in Table 2.

TABLE 2

| Compound | Physical properties |
|---|---|
| N-(4-Trifluoromethylbenzyl)-2-chloro-5-nitrobenzamide | m.p. 181° C. |
| Methyl(R)-2-(2-chloro-5-nitrobenzoylamino)-2-(4-(3-chloro-5-trifluoromethyl-2-pyridyloxy)phenyl)acetate | m.p. 184-186° C. |
| Methy(S)-2-(2-chloro-5-nitrobenzoylamino)-2-(4-(3-chloro-5-trifluoromethyl-2-pyridyloxy)phenyl)acetate | m.p. 184-185° C. |
| N-(4-(6-Chloro-4-trifluoromethyl-2-pyridyloxy)cyclohexyl)-2-chloro-5-nitrobenzamide | m.p. 232-233° C. |
| N-(2-(4-(3-Chloro-5-trifluoromethyl-2-pyridyloxy)phenyl)ethyl)-2-chloro-5-nitrobenzamide | m.p. 172-174° C. |
| N-(1-(3-Chloro-5-trifluoromethyl-2-pyridyl)-4-piperidinylmethyl)-2-chloro-5-nitrobenzamide | m.p. 183-184° C. |
| N-(2-(3-Chloro-5-trifluoromethyl-2-pyridyloxy)ethyl)-2-chloro-5-nitrobenzamide | m.p. 126-127° C. |
| N-(4-(3-Chloro-5-trifluoromethyl-2-pyridyloxy)benzyl)-2-chloro-5-nitrobenzamide | m.p. 169° C. |
| N-(1-(3-Chloro-5-trifluoromethyl-2-pyridyl)-4-piperidinyl)-2-chloro-5-nitrobenzamide | m.p. 193° C. |
| N-(3-(3-Chloro-5-trifluoromethyl-2-pyridyloxy)propyl)-2-chloro-5-nitrobenzamide | m.p. 147° C. |
| N-(4-(3-Chloro-5-trifluoromethyl-2-pyridyloxy)butyl)-2-chloro-5-nitrobenzamide | m.p. 103° C. |
| N-(4-(3-Chloro-5-trifluoromethyl-2-pyridyloxy)-2-buten-1-yl)-2-chloro-5-nitrobenzamide | m.p. 157° C. |
| N-(4-(3-Chloro-5-trifluoromethyl-2-pyridyloxy)-2-butyn-1-yl)-2-chloro-5-nitrobenzamide | m.p. 163° C. |
| N-(4-(3-Chloro-5-trifluoromethyl-2-pyridyloxy)cyclohexylmethyl)-2-chloro-5-nitrobenzamide | Solid |
| N-(3-(1-Adamantylamino)propyl)-2-chloro-5-nitrobenzamide | m.p. 83-85° C. |
| N-(4-(6-Chloro-4-trifluoromethyl-2-pyridyloxy)-2-buten-1-yl)-2-chloro-5-nitrobenzamide | m.p. 134-138° C. |
| N-(4-(6-Chloro-4-trifluoromethyl-2-pyridyloxy)-2-butyn-1-yl)-2-chloro-5-nitrobenzamide | m.p. 173-176° C. |

TABLE 2-continued

| Compound | Physical properties |
|---|---|
| N-(4-(6-Chloro-4-trifluoromethyl-2-pyridyloxy)cyclohexylmethyl)-2-chloro-5-nitrobenzamide | m.p. 148-151° C. |
| N-(2-(6-Chloro-4-trifluoromethyl-2-pyridyloxy)ethyl)-2-chloro-5-nitrobenzamide | m.p. 149-152° C. |
| N-(3-(6-Chloro-4-trifluoromethyl-2-pyridyloxy)propyl)-2-chloro-5-nitrobenzamide | m.p. 144-145° C. |
| N-(4-(6-Chloro-4-trifluoromethyl-2-pyridyoxy)butyl)-2-chloro-5-nitrobenzamide | m.p. 114-115° C. |
| N-(1-(6-chloro-4-trifluoromethyl-2-pyridyl)-4-piperidinylmethyl)-2-chloro-5-nitrobenzamide | m.p. 189-191° C. |
| N-(3-(3-Chloro-5-trifluoromethyl-2-pyridylthio)propyl)-2-chloro-5-nitrobenzamide | m.p. 140-142° C. |
| N-(4-(6-chloro-4-trifluoromethyl-2-pyridyloxy)benzyl)-2-chloro-5-nitrobenzamide | m.p. 170-174° C. |
| N-(2-(6-Morpholino-4-trifluoromethyl-2-pyridyloxy)ethyl)-2-chloro-5-nitrobenzamide | m.p. 190-193° C. |
| cis-N-(4-(6-Chloro-4-trifluoromethyl-2-pyridyloxy)-2-buten-1-yl)-2-chloro-5-nitrobenzamide | m.p. 142-146° C. |
| N-(3-(6-(4-Methylpiperazino)-4-trifluoromethyl-2-pyridyloxy)propyl)-2-chloro-5-nitrobenzamide | m.p. 128-130° C. |
| N-(2-(2-(6-Chloro-4-trifluoromethyl-2-pyridyloxy)ethoxy)ethyl)-2-chloro-5-nitrobenzamide | m.p. 79-82° C. |
| N-(2-(6-(4-Methylpiperazino)-4-trifluoromethyl-2-pyridyloxy)ethyl)-2-chloro-5-nitrobenzamide | m.p. 126-128° C. |
| N-(3-(6-Dimethylamino-4-trifluoromethyl-2-pyridyloxy)propyl)-2-chloro-5-nitrobenzamide | m.p. 126-128° C. |
| N-(2-(6-Dimethylamino-4-trifluoromethyl-2-pyridyloxy)ethyl)-2-chloro-5-nitrobenzamide | m.p. 126-128° C. |
| N-(3-(3-Chloro-5-trifluoromethyl-2-pyridylsulfinyl)propyl)-2-chloro-5-nitrobenzamide | m.p. 133-137° C. |
| N-(3-(3-Chloro-5-trifluoromethyl-2-pyridylsulfonyl)propyl)-2-chloro-5-nitrobenzamide | m.p. 140-142° C. |
| N-(3-(6-Morpholino-4-trifluoromethyl-2-pyridyloxy)propyl)-2-chloro-5-nitrobenzamide | m.p. 155-156° C. |
| N-(4-(6-Morpholino-4-trifluoromethyl-2-pyridyloxy)butyl)-2-chloro-5-nitrobenzamide | m.p. 132-136° C. |
| N-(4-(6-Dimethylamino-4-trifluoromethyl-2-pyridyloxy)butyl)-2-chloro-5-nitrobenzamide | m.p. 106-107° C. |
| N-(4-(6-(4-Methylpiperazino)-4-trifluoromethyl-2-pyridyloxy)butyl)-2-chloro-5-nitrobenzamide | m.p. 146-148° C. |
| N-(2-(6-Chloro-4-trifluoromethyl-2-pyridylamino)ethyl)-2-chloro-5-nitrobenzamide | m.p. 210-212° C. |
| N-(3-(6-Chloro-4-trifluoromethyl-2-pyridylamino)propyl)-2-chloro-5-nitrobenzamide | m.p. 137-138° C. |
| N-(4-(6-Chloro-4-trifluoromethyl-2-pyridylamino)butyl)-2-chloro-5-nitrobenzamide | m.p. 150-152° C. |
| N-(2-(6-Chloro-4-trifluoromethyl-2-pyridyloxy)ethylaminocarbonylmethyl)-2-chloro-5-nitrobenzamide | m.p. 167-169° C. |
| N-(2-(2-(6-Chloro-4-trifluoromethyl-2-pyridyloxy)ethylthio)ethyl)-2-chloro-5-nitrobenzamide | m.p. 97-98° C. |
| N-(2-(2-(6-Chloro-4-trifluoromethyl-2-pyridyloxy)ethylsulfinyl)ethyl)-2-chloro-5-nitrobenzamide | m.p. 118-120° C. |
| N-(2-(2-(6-Chloro-4-trifluoromethyl-2-pyridyloxy)ethylsulfonyl)ethyl)-2-chloro-5-nitrobenzamide | m.p. 104-107° C. |
| N-(3-(2-Chloro-4-trifluoromethylphenoxy)propyl)-2-chloro-5-nitrobenzamide | m.p. 141-143° C. |
| N-(3-(6-Amino-4-trifluoromethyl-2-pyridyloxy)propyl)-2-chloro-5-nitrobenzamide | m.p. 110-113° C. |
| N-(3-(3-Chloro-5-trifluoromethyl-2-pyridylamino)propyl)-2-chloro-5-nitrobenzamide | m.p. 133-135° C. |
| N-(3-(6-Methylamino-4-trifluoromethyl-2-pyridyloxy)propyl)-2-chloro-5-nitrobenzamide | m.p. 154-157° C. |
| N-(2-(6-Chloro-4-trifluoromethyl-2-pyridylthio)ethyl)-2-chloro-5-nitrobenzamide | m.p. 161-163° C. |
| N-(3-(6-Methoxy-4-trifluoromethyl-2-pyridyloxy)propyl)-2-chloro-5-nitrobenzamide | m.p. 115-117° C. |
| N-(3-(6-Chloro-4-trifluoromethyl-2-pyridylthio)propyl)-2-chloro-5-nitrobenzamide | m.p. 131-132° C. |
| N-(2-(6-Methoxy-4-trifluoromethyl-2-pyridyloxy)ethyl)-2-chloro-5-nitrobenzamide | m.p. 137-139° C. |
| N-(5-(6-Chloro-4-trifluoromethyl-2-pyridyloxy)pentyl)-2-chloro-5-nitrobenzamide | m.p. 102-103° C. |
| N-(3-(6-(2-Propylamino)-4-trifluoromethyl-2-pyridyloxy)propyl)-2-chloro-5-nitrobenzamide | m.p. 111-113° C. |
| N-(3-(6-(1-Butylamino)-4-trifluoromethyl-2-pyridyloxy)propyl)-2-chloro-5-nitrobenzamide | m.p. 91-93° C. |
| N-(3-(6-Acetylamino-4-trifluoromethyl-2-pyridyloxy)propyl)-2-chloro-5-nitrobenzamide | m.p. 153-154° C. |
| N-(4-(6-Methoxy-4-trifluoromethyl-2-pyridyloxy)butyl)-2-chloro-5-nitrobenzamide | m.p. 117-120° C. |
| N-(4-(6-Chloro-4-trifluoromethyl-2-pyridylthio)butyl)-2-chloro-5-nitrobenzamide | m.p. 136-137° C. |
| N-(3-(6-Chloro-4-trifluoromethyl-2-pyridyloxy)propyl)-2-chloro-4,5-dinitrobenzamide | m.p. 159° C. |
| N-(3-(6-Chloro-4-trifluoromethyl-2-pyridyloxy)propyl)-4-amino-2-chloro-5-nitrobenzamide | m.p. 175-178° C. |
| N-(3-(6-Phenylamino-4-trifluoromethyl-2-pyridyloxy)propyl)-2-chloro-5-nitrobenzamide | Amorphous solid |
| N-(3-(3-Chloro-5-trifluoromethyl-2-pyridylamino)propyl)-2-fluoro-5-nitrobenzamide | m.p. 143-144° C. |
| N-(3-(3-Chloro-5-trifluoromethyl-2-pyridyloxy)-2,2-dimethylpropyl)-2-chloro-5-nitrobenzamide | m.p. 93-94° C. |
| N-(3-(6-Chloro-4-trifluoromethyl-2-pyridyloxy)-2,2-dimethylpropyl)-2-chloro-5-nitrobenzamide | m.p. 82-84° C. |
| N-(3-(3-Chloro-5-trifluoromethyl-2-pyridylamino)-2,2-dimethylpropyl)-2-chloro-5-nitrobenzamide | m.p. 65-69° C. |
| N-(3-(6-Chloro-4-trifluoromethyl-2-pyridyloxy)propyl)-2-chloro-4-methylamino-5-nitrobenzamide | m.p. 156-158° C. |
| N-(3-(3-Trifluoromethyl-2-pyridylsulfinylamino)propyl)-2-chloro-5-nitrobenzamide | Oil |

TABLE 2-continued

| Compound | Physical properties |
|---|---|
| N-(3-(6-Chloro-4-trifluoromethyl-2-pyridyloxy)propyl)-2-fluoro-5-nitrobenzamide | m.p. 100-102° C. |
| N-(3-(3-Chloro-5-trifluoromethyl-2-pyridyloxy)propyl)-2-fluoro-5-nitrobenzamide | m.p. 126-127° C. |
| N-(3-(6-Methoxy-4-trifluoromethyl-2-pyridyloxy)propyl)-2-fluoro-5-nitrobenzamide | m.p. 96-98° C. |
| N-(3-(3-Chloro-5-trifluoromethyl-2-pyridyloxy)-2,2-dimethylpropyl)-2-fluoro-5-nitrobenzamide | Oil |
| N-(3-(6-Chloro-4-trifluoromethyl-2-pyridyloxy)-2,2-dimethylpropyl)-2-fluoro-5-nitrobenzamide | Oil |
| N-(3-(3-Chloro-5-trifluoromethyl-2-pyridylamino)-2,2-dimethylpropyl)-2-fluoro-5-nitrobenzamide | m.p. 46-50° C. |
| N-(3-(3-Chloro-5-trifluoromethyl-2-pyridylthio)propyl)-2-fluoro-5-nitrobenzamide | m.p. 132-134° C. |
| N-(3-(6-Chloro-4-trifluoromethyl-2-pyridylthio)propyl)-2-fluoro-5-nitrobenzamide | m.p. 80-81° C. |
| N-(3-(6-Ethoxy-4-trifluoromethyl-2-pyridyloxy)propyl)-2-fluoro-5-nitrobenzamide | m.p. 58-60° C. |
| N-(3-(6-Isopropoxy-4-trifluoromethyl-2-pyridyloxy)propyl)-2-fluoro-5-nitrobenzamide | Oil |
| N-(4-(3-Chloro-5-trifluoromethyl-2-pyridyloxy)phenyl)-4-chloronicotinamide | m.p. 178-180° C. (decomposition) |
| N-(4-(6-Chloro-4-trifluoromethyl-2-pyridyloxy)phenyl)-4-chloronicotinamide | m.p. 217-218° C. (decomposition) |
| N-(4-(1-Adamantyl)-2-methylphenyl)-4-chloronicotinamide | Amorphous solid |
| N-(3-(6-Chloro-4-trifluoromethyl-2-pyridyloxy)propyl-4-chloronicotinamide | m.p. 86-87° C. |
| N-(4-(6-Chloro-4-trifluoromethyl-2-pyridyloxy)butyl)-4-chloronicotinamide | m.p. 118-119° C. |
| N-(3-(2-Chloro-4-trifluoromethylphenoxy)propyl)-4-chloronicotinamide | m.p. 140-143° C. |
| N-(3-(6-Methylamino-4-trifluoromethyl-2-pyriyloxy)propyl)-4-chloronicotinamide | m.p. 117-118° C. |
| N-(3-(6-Amino-4-trifluoromethyl-2-pyridyloxy)propyl)-4-chloronicotinamide | m.p. 101-102° C. |
| N-(3-(3-Chloro-5-trifluoromethyl-2-pyridylamino)propyl)-4-chloronicotinamide | m.p. 112-113° C. |
| N-(4-(3-Chloro-5-trifluoromethyl-2-pyridyloxy)phenyl)-2,4-dichloronicotinamide | m.p. 226-227° C. |
| N-(3-(6-Chloro-4-trifluoromethyl-2-pyridyloxy)propyl)-2,4-dichloronicotinamide | m.p. 96° C. |
| N-(4-(3-Chloro-5-trifluoromethyl-2-pyridyloxy)phenyl)-2,4-dichloro-6-methylnicotinamide | m.p. 210-213° C. |
| N-(5-(6-Chloro-4-trifluoromethyl-2-pyridyloxy)pentyl)-4-chloronicotinamide | m.p. 60-61° C. |
| N-(3-(6-Acetylamino-4-trifluoromethyl-2-pyridyloxy)propyl)-4-chloronicotinamide | m.p. 140-142° C. |
| N-(3-(6-(1-Butylamino)-4-trifluoromethyl-2-pyridyloxy)propyl)-4-chloronicotinamide | m.p. 82-83° C. |
| N-(4-(3-Chloro-5-trifluoromethyl-2-pyridyloxy)phenyl)-4-chloro-1,3-dimethylpyrazolo[3,4-b]pyridine-5-carboxamide | m.p. 85-88° C. |
| N-(4-(3-Chloro-5-trifluoromethyl-2-pyridyloxy)phenyl)-4,6-dichloronicotinamide | m.p. 209-211° C. |
| N-(4-(3-Chloro-5-trifluoromethyl-2-pyridyloxy)phenyl)-4,6-dichloro-5-methylnicotinamide | m.p. 184° C. |
| N-(4-(3-Chloro-5-trifluoromethyl-2-pyridyloxy)phenyl)-4-chloroquinoline-3-carboxamide | m.p. 216° C. |
| N-(4-(3-Chloro-5-trifluoromethyl-2-pyridyloxy)phenyl)-4-chloro-2,6-dimethylnicotinamide | m.p. 221-223° C. |
| N-(3-(6-Chloro-4-trifluoromethyl-2-pyridyloxy)propyl)-4,6-dichloronicotinamide | m.p. 96-97° C. |
| N-(4-(3-Chloro-5-trifluoromethyl-2-pyridyloxy)phenyl)-4-chloronicotinamide-1-oxide | m.p. 218-219° C. |
| N-(4-(3-Chloro-5-trifluoromethyl-2-pyridyloxy)-3-methylphenyl)-4-chloronicotinamide | m.p. 167-170° C. (decomposition) |
| N-(4-(6-Chloro-4-trifluoromethyl-2-pyridylthio)phenyl)-4-chloronicotinamide | m.p. 186-190° C. (decomposition) |
| N-(4-(3-Chloro-5-trifluoromethyl-2-pyridylamino)phenyl)-4-chloronicotinamide | m.p. 180-182° C. (decomposition) |
| N-(4-(3,5-Dichloro-2-pyridyloxy)phenyl)-4-chloronicotinamide | m.p. 165-168° C. (decomposition) |
| N-(2-(2-Adamantyloxy)-5-pyridyl)-4-chloronicotinamide | Amorphous solid |
| N-(4-(3-Chloro-5-trifluoromethyl-2-pyridyloxy)-3,5-dimethylphenyl)-4-chloronicotinamide | m.p. 188-192° C. |
| N-(4-(3-Chloro-5-trifluoromethyl-2-pyridyloxy)-3-(1-pyrrolyl)phenyl)-4-chloronicotinamide | m.p. 138-140° C. |
| N-(4-(1-Adamantyloxy)phenyl)-4-chloronicotinamide | m.p. 85-88° C. |
| N-(3-(5-Bromo-2-pyrimidinylamino)propyl)-2-chloro-5-nitrobenzamide | m.p. 178-180° C. |
| N-(3-(5-Bromo-2-pyrimidinylamino)propyl)-2-fluoro-5-nitrobenzamide | m.p. 157-159° C. |
| N-(3-(4-Trifluoromethyl-2-pyrimidinylamino)propyl)-2-chloro-5-nitrobenzamide | m.p. 141-143° C. |
| cis-N-(4-(3-Chloro-5-trifluoromethyl-2-pyridyloxy)-2-buten-1-yl)-2-fluoro-5-nitrobenzamide | m.p. 102-103° C. |
| cis-N-(4-(6-Chloro-4-trifluoromethyl-2-pyridyloxy)-2-buten-1-yl)-2-fluoro-5-nitrobenzamide | m.p. 103-104° C. |
| N-(4-1-Adamantylamino)phenyl)-4-chloronicotinamide | m.p. 138-140° C. |
| N-(3-(6-Dimethylamino-4-trifluoromethyl-2-pyridyloxy)propyl)-2-fluoro-5-nitrobenzamide | m.p. 80-82° C. |
| N-(3-(6-Dimethylamino-4-trifluoromethyl-2-pyridyloxy)propyl)-2,4-dichloro-5-nitrobenzamide | m.p. 126-127° C. |
| N-(3-(6-Dimethylamino-4-trifluoromethyl-2-pyridyloxy)propyl)-2-chloro-5-cyanobenzamide | m.p. 112-133° C. |
| N-(3-(6-Dimethylamino-4-trifluoromethyl-2-pyridyloxy)propyl)-4-chloronicotinamide | m.p. 107° C. |
| N-(3-(6-Dimethylamino-4-trifluoromethyl-2-pyridyloxy)propyl)-2-chloro-4-amino-5-nitrobenzamide | m.p. 162-163° C. |

TABLE 2-continued

| Compound | Physical properties |
|---|---|
| N-(3-(6-Dimethylamino-4-trifluoromethyl-2-pyridyloxy)propyl)-2-chloro-4-methoxy-5-nitrobenzamide | m.p. 133-134° C. |
| N-(3-(6-(1-Pyrrolidino)-4-trifluoromethyl-2-pyridyloxy)propyl)-2-fluoro-5-nitrobenzamide | m.p. 114-115° C. |
| N-(3-(6-(1H-Pyrrol-1-yl)-4-trifluoromethyl-2-pyridyloxy)propyl)-2-fluoro-5-nitrobenzamide | m.p. 115-118° C. |
| N-(3-(6-(1-Pyrrolidino)-4-trifluoromethyl-2-pyridyloxy)propyl)-2-chloro-5-nitrobenzamide | m.p. 150-151° C. |
| N-(3-(6-(1H-Pyrrol-1-yl)-4-trifluoromethyl-2-pyridyloxy)propyl)-2-chloro-5-nitrobenzamide | m.p. 118-120° C. |
| N-(3-(6-(1-Pyrrolidino)-4-trifluoromethyl-2-pyridyloxy)propyl)-2-chloro-5-cyanobenzamide | m.p. 145-147° C. |
| N-(3-(6-(1H-Pyrrol-1-yl)-4-trifluoromethyl-2-pyridyloxy)propyl)-2-chloro-5-cyanobenzamide | m.p. 157-159° C. |
| N-(3-(6-(1-Pyrrolidino)-4-trifluoromethyl-2-pyridyloxy)propyl)-4-chloronicotinamide | m.p. 106-107° C. |
| N-(3-(6-(1H-Pyrrol-1-yl)-4-trifluoromethyl-2-pyridyloxy)propyl)-4-chloronicotinamide | m.p. 112-113° C. |
| N-(3-(4-Trifluoromethyl-2-pyrimidinylamino)propyl)-2-fluoro-5-nitrobenzamide | m.p. 110-111° C. |
| N-(4-(3-Chloro-5-trifluoromethyl-2-pyridyloxy)-2-butyn-1-yl)-2-fluoro-5-nitrobenzamide | m.p. 151-154° C. |
| N-(4-(6-Chloro-4-trifluoromethyl-2-pyridyloxy)-2-butyn-1-yl)-2-fluoro-5-nitrobenzamide | m.p. 146-149° C. |
| N-(4-(4,6-Bistrifluoromethyl-2-pyridyloxy)phenyl)-4-chloronicotinamide | m.p. 207-216° C. (decomposition) |
| N-(4-(3-Chloro-5-trifluoromethyl-2-pyridylthio)phenyl)-4-chloronicotinamide | m.p. 178-179° C. |
| N-(3-(3-(1H-Pyrrol-1-yl)-5-trifluoromethyl-2-pyridyloxy)propyl)-2-chloro-5-nitrobenzamide | m.p. 140-143° C. |
| N-(3-(3-(1H-Pyrrol-1-yl)-5-trifluoromethyl-2-pyridyloxy)propyl)-2-fluoro-5-nitrobenzamide | m.p. 108° C. |
| N-(3-(3-(1H-Pyrrol-1-yl)-5-trifluoromethyl-2-pyridyloxy)propyl)-2-chloro-5-cyanobenzamide | m.p. 158-159° C. |
| N-(3-(3-(1H-Pyrrol-1-yl)-5-trifluoromethyl-2-pyridyloxy)propyl)-4-chloronicotinamide | m.p. 121-122° C. |
| N-(3,5,6-Trifluoro-2-pyridyloxy)propyl)-2-chloro-5-nitrobenzamide | m.p. 121° C. |
| N-(3,5,6-Trifluoro-2-pyridyloxy)propyl)-2-fluoro-5-nitrobenzamide | m.p. 81-82° C. |
| N-(3,5,6-Trifluoro-2-pyridyloxy) propyl)-2-chloro-5-cyanobenzamide | m.p. 121-122° C. |
| N-(3,5,6-Trifluoro-2-pyridyloxy)propyl)-4-chloronicotinamide | m.p. 103-105° C. |
| N-(3-(3,6-Dichloro-5-trifluoromethyl-2-pyridylamino)propyl)-2-chloro-5-nitrobenzamide | m.p. 172-174° C. |
| N-(3-(3,6-Dichloro-5-trifluoromethyl-2-pyridylamino)propyl)-2-fluoro-5-nitrobenzamide | m.p. 115-117° C. |
| N-(3-(6-Trifluoromethyl-2-pyridyloxy)propyl)-2-chloro-5-nitrobenzamide | m.p. 108-111° C. |
| N-(3-(6-Trifluoromethyl-2-pyridyloxy)propyl)-2-fluoro-5-nitrobenzamide | m.p. 86-87° C. |
| N-(3-(6-Trifluoromethyl-2-pyridylamino)propyl)-2-fluoro-5-nitrobenzamide | Oil |
| N-(3-(6-Trifluoromethyl-2-pyridylamino)propyl)-2-chloro-5-nitrobenzamide | Oil |
| N-(3-(3,6-Dichloro-5-trifluoromethyl-2-pyridyloxy)propyl)-2-chloro-5-nitrobenzamide | m.p. 145-147° C. |
| N-(3-(5-Chloro-3-trifluoromethyl-2-pyridylamino)propyl)-2-chloro-5-nitrobenzamide | m.p. 151-152° C. |
| N-(3-(5-Chloro-3-trifluoromethyl-2-pyridylamino)propyl)-2-fluoro-5-nitrobenzamide | m.p. 105-107° C. |
| N-(3-(3,6-Dichloro-5-trifluoromethyl-2-pyridyloxy)propyl)-2-fluoro-5-nitrobenzamide | m.p. 133-135° C. |
| N-(3-(6-Isopropoxy-4-trifluoromethyl-2-pyridyloxy)propyl)-2-Chloro-5-cyanobenzamide | m.p. 55-56° C. |
| N-(3-(6-(1-Propyloxy)-4-trifluoromethyl-2-pyridyloxy)propyl)-2-fluoro-5-nitrobenzamide | Oil |
| N-(3-(6-(1-Butyloxy)-4-trifluoromethyl-2-pyridyloxy)propyl)-2-fluoro-5-nitrobenzamide | Oil |
| N-(3-(2-Fluoro-4-trifluoromethylphenyloxy)propyl)-2-chloro-5-nitrobenzamide | m.p. 126-127° C. |
| N-(3-(2-Fluoro-4-trifluoromethylphenyloxy)propyl)-2-fluoro-5-nitrobenzamide | m.p. 99° C. |
| N-(3-Phenoxypropyl)-2-chloro-5-nitrobenzamide | m.p. 114-115° C. |
| N-(3-Phenoxypropyl)-2-fluoro-5-nitrobenzamide | m.p. 74-76° C. |
| N-(3-Phenylthiopropyl)-2-chloro-5-nitrobenzamide | m.p. 113° C. |
| N-(3-Phenylthiopropyl)-2-fluoro-5-nitrobenzamide | m.p. 71-72° C. |
| N-(3-(3,5-Bistrifluoromethylphenyloxy)propyl)-2-chloro-5-nitrobenzamide | m.p. 115° C. |
| N-(3-(3,5-Bistrifluoromethylphenyloxy)propyl)-2-fluoro-5-nitrobenzamide | m.p. 104-105° C. |
| N-(3-(6-Thiomorpholino-4-trifluoromethyl-2-pyridyloxy)propyl)-2-chloro-5-nitrobenzamide | m.p. 132-134° C. |
| N-(3-(6-Thiomorpholino-4-trifluoromethyl-2-pyridyloxy)propyl)-2-fluoro-5-nitrobenzamide | m.p. 128-130° C. |
| N-(3-(6-Thiomorpholino-4-trifluoromethyl-2-pyridyloxy)propyl)-2-chloro-5-cyanobenzamide | m.p. 143-144° C. |
| N-(3-(6-Thiomorpholino-4-trifluoromethyl-2-pyridyloxy)propyl)-4-chloronicotinamide | m.p. 113-115° C. |
| N-(3-(6-Piperidino-4-trifluoromethyl-2-pyridyloxy)propyl)-2-chloro-5-nitrobenzamide | m.p. 142-144° C. |
| N-(3-(6-Piperidino-4-trifluoromethyl-2-pyridyloxy)propyl)-2-fluoro-5-nitrobenzamide | m.p. 99-100° C. |
| N-(3-(6-Piperidino-4-trifluoromethyl-2-pyridyloxy)propyl)-2-chloro-5-cyanobenzamide | m.p. 129-130° C. |
| N-(3-(6-Piperidino-4-trifluoromethyl-2-pyridyloxy)propyl)-4-chloronicotinamide | m.p. 88-90° C. |

TABLE 2-continued

| Compound | Physical properties |
|---|---|
| N-(3-(5-Chloro-3-trifluoromethyl-2-pyridyloxy)propyl)-2-chloro-5-nitrobenzamide | m.p. 141-143° C. |
| N-(3-(5-Chloro-3-trifluoromethyl-2-pyridyloxy)propyl)-2-fluoro-5-nitrobenzamide | m.p. 100-102° C. |
| N-(3-(4,5-Bistrifluoromethyl-2-pyridyloxy)propyl)-2-chloro-5-nitrobenzamide | m.p. 130-131° C. |
| N-(3-(4,5-Bistrifluoromethyl-2-pyridyloxy)propyl)-2-fluoro-5-nitrobenzamide | m.p. 78-80° C. |
| N-(3-(4,5-Bistrifluoromethyl-2-pyridylamino)propyl)-2-chloro-5-nitrobenzamide | m.p. 117-120° C. |
| N-(3-(4,5-Bistrifluoromethyl-2-pyridylamino)propyl)-2-fluoro-5-nitrobenzamide | m.p. 140-143° C. |
| N-(4-(3-Chloro-5-trifluoromethyl-2-pyridylamino)phenyl)-4,6-dichloronicotinamide | m.p. 188-191° C. |
| N-(4-(6-Chloro-4-trifluoromethyl-2-pyridyloxy)phenyl)-4,6-dichloronicotinamide | m.p. 208-210° C. |
| N-(4-(3-Chloro-5-trifluoromethyl-2-pyridyloxy)-2-fluorophenyl)-4,6-dichloronicotinamide | m.p. 171-173° C. |
| N-(4-(6-Chloro-4-trifluoromethyl-2-pyridyloxy)-2-fluorophenyl)-4,6-dichloronicotinamide | m.p. 203-204° C. |
| N-(3-(8-Quinolinyloxy)propyl)-2-chloro-5-nitrobenzamide | m.p. 143-145° C. |
| N-(4-(4,6-Dimethoxy-2-pyrimidinyloxy)-2-butyn-1-yl)-2-chloro-5-nitrobenzenesulfonamide | m.p. 149-151° C. |
| N-(3-(2-Quinolinyloxy)propyl)-2-chloro-5-nitrobenzamide | m.p. 128-129° C. |
| N-(3-(8-Quinolinyloxy)propyl)-2-fluoro-5-nitrobenzamide | m.p. 123-126° C. |
| N-(3-(2-Thiazolylthio)propyl)-2-chloro-5-nitrobenzamide | m.p. 82-83° C. |
| N-(3-(1-Methyl-5-tetrazolylthio)propyl)-2-chloro-5-nitrobenzamide | Amorphous solid |
| N-(3-(3,5-Dichloro-2-pyridyloxy)propyl)-2-chloro-5-nitrobenzamide | m.p. 130-132° C. |
| N-(3-(3,5-Dichloro-2-pyridyloxy)propyl)-2-fluoro-5-nitrobenzamide | m.p. 130-132° C. |
| N-(3-(5-Bromo-2-pyrimidinyloxy)propyl)-2-chloro-5-nitrobenzamide | m.p. 145-146° C. |
| N-(3-(5-Bromo-2-pyrimidinyloxy)propyl)-2-fluoro-5-nitrobenzamide | m.p. 133-135° C. |
| N-(3-(2-Pyrimidinylthio)propyl)-2-fluoro-5-nitrobenzamide | m.p. 97-98° C. |
| N-(3-(2-Pyrimidinylthio)propyl)-2-chloro-5-nitrobenzamide | m.p. 105-106° C. |
| N-(4-(3,5-Bistrifluoromethylphenoxy)-2-butyn-1-yl)-2-chloro-5-nitrobenzenesulfonamide | m.p. 98-99° C. |
| N-(3-(2-Pyrimidinyloxy)propyl)-2-fluoro-5-nitrobenzamide | m.p. 112-113° C. |
| N-(4-(4-Phenylthiazol-2-ylthio)-2-butyn-1-yl)-2-chloro-5-nitrobenzenesulfonamide | Amorphous solid |
| N-(3-(2-Pyrimidinylamino)propyl)-2-chloro-5-nitrobenzamide | m.p. 170-172° C. |
| N-(3-(2-Benzothiazolylthio)propyl)-2-chloro-5-nitrobenzamide | m.p. 120-121° C. |
| N-(3-(2-Benzothiazolylthio)propyl)-2-fluoro-5-nitrobenzamide | m.p. 67-68° C. |
| N-(3-(6-Dimethylamino-4-trifluoromethyl-2-pyridyloxy)propyl)-2-chloro-5-nitrobenzenesulfonamide | Oil |
| N-(3-(6-(1-Pyrrolidino)-4-trifluoromethyl-2-pyridyloxy)propyl)-2-chloro-5-nitrobenzenesulfonamide | Oil |
| N-(4-(3-Chloro-5-trifluoromethyl-2-pyridylamino)cyclohexyl)-2-chloro-5-nitrobenzamide | m.p. 177-178° C. |
| N-(3-(2,6-Dichloro-4-trifluoromethylphenyloxy)propyl)-2-chloro-5-nitrobenzamide | m.p. 155° C. |
| N-(3-(2,6-Dichloro-4-trifluoromethylphenyloxy)propyl)-2-fluoro-5-nitrobenzamide | m.p. 116-117° C. |
| N-(3-(3-Trifluoromethylphenyloxy)propyl)-2-chloro-5-nitrobenzamide | m.p. 92-93° C. |
| N-(3-(3-Trifluoromethylphenyloxy)propyl)-2-fluoro-5-nitrobenzamide | m.p. 75° C. |
| N-(3-(4-Cyano-3-trifluoromethylphenyloxy)propyl)-2-chloro-5-nitrobenzamide | m.p. 154-155° C. |
| N-(3-(4-Cyano-3-trifluoromethylphenyloxy)propyl)-2-fluoro-5-nitrobenzamide | m.p. 123-124° C. |
| N-(3-(3,4-Dichlorophenyloxy)propyl)-2-chloro-5-nitrobenzamide | m.p. 121° C. |
| N-(3-(3,4-Dichlorophenyloxy)propyl)-2-fluoro-5-nitrobenzamide | m.p. 134-135° C. |
| N-(3-(6-(2,2,2-Trifluoroethyloxy)-4-trifluoromethyl-2-pyridyloxy)propyl)-2-chloro-5-nitrobenzamide | m.p. 107-108° C. |
| N-(3-(6-(2,2,2-Trifluoroethyloxy)-4-trifluoromethyl-2-pyridyloxy)propyl)-2-fluoro-5-nitrobenzamide | m.p. 106-107° C. |
| N-(3-(6-Isopropoxy-4-trifluoromethyl-2-pyridyloxy)propyl)-2-chloro-5-nitrobenzamide | m.p. 73-74° C. |
| N-(3-(6-Ethoxy-4-trifluoromethyl-2-pyridyloxy)propyl)-2-chloro-5-nitrobenzamide | m.p. 55-56° C. |
| N-(3-(6-(1-Propyloxy)-4-trifluoromethyl-2-pyridyloxy)propyl)-2-chloro-5-nitrobenzamide | m.p. 105-106° C. |
| N-(3-(6-(1-Butyloxy)-4-trifluoromethyl-2-pyridyloxy)propyl)-2-chloro-5-nitrobenzamide | m.p. 92-93° C. |
| N-(4-(3-Chloro-5-trifluoromethyl-2-pyridyloxy-2-butyn-1-yl)-4,6-dichloronicotinamide | m.p. 166-167° C. |
| cis-N-(4-(3-Chloro-5-trifluoromethyl-2-pyridyloxy)-2-buten-1-yl)-4,6-dichloronicotinamide | m.p. 119-120° C. |
| N-(4-(2,6-Dimethoxy-4-pyrimidinyloxy)-2-butyn-1-yl)-2-chloro-5-nitrobenzenesulfonamide | m.p. 167-169° C. |
| N-(3-(3,5-Bistrifluoromethyl-2-pyridyloxy)propyl)-2-chloro-5-nitrobenzamide | m.p. 146-149° C. |
| N-(3-(3,5-Bistrifluoromethyl-2-pyridyloxy)propyl)-2-fluoro-5-nitrobenzamide | m.p. 117-118° C. |
| N-(3-(2,6-Bistrifluoromethyl-4-pyridyloxy)propyl)-2-chloro-5-nitrobenzamide | m.p. 134-135° C. |
| N-(3-(2,6-Bistrifluoromethyl-4-pyridyloxy)propyl)-2-fluoro-5-nitrobenzamide | m.p. 87-89° C. |
| N-(3-(3,5-Dichloro-2-pyridylamino)propyl)-2-fluoro-5-nitrobenzamide | m.p. 125-127° C. |
| N-(3-(3,5-Dichloro-2-pyridylamino)propyl)-2-chloro-5-nitrobenzamide | m.p. 133-135° C. |

TABLE 2-continued

| Compound | Physical properties |
|---|---|
| N-(3-(6-(2-Methoxyethyloxy)-4-trifluoromethyl-2-pyridyloxy)propyl)-2-chloro-5-nitrobenzamide | m.p. 105-106° C. |
| N-(3-(6-(2-Methoxyethyloxy)-4-trifluoromethyl-2-pyridyloxy)propyl)-2-fluoro-5-nitrobenzamide | m.p. 84-88° C. |
| N-(3-(6-(2,2-Dimethoxyethyloxy)-4-trifluoromethyl-2-pyridyloxy)propyl)-2-chloro-5-nitrobenzamide | m.p. 97-99° C. |
| N-(3-(6-(2,2-Dimethoxyethyloxy)-4-trifluoromethyl-2-pyridyloxy)propyl)-2-fluoro-5-nitrobenzamide | m.p. 66-68° C. |
| N-(3-(1-Methyl-5-tetrazolylthio)propyl)-2-fluoro-5-nitrobenzamide | m.p. 104-107° C. |
| N-(3-(1-Benzotriazolyloxy)propyl)-2-chloro-5-nitrobenzamide | m.p. 116-118° C. |
| N-(3-(4-Ethoxycarbonylphenyloxy)propyl)-2-chloro-5-nitrobenzamide | m.p. 118-119° C. |
| N-(3-(4-Ethoxycarbonyl-2-pyridyloxy)propyl)-2-chloro-5-nitrobenzamide | m.p. 154-155° C. |
| N-(4-(3-Chloro-5-trifluoromethyl-2-pyridyloxy)-3-methylphenyl)-4,6-dichloronicotinamide | m.p. 196-198° C. |
| N-(4-(3-Chloro-5-trifluoromethyl-2-pyridylmethoxy)phenyl)-4,6-dichloronicotinamide | m.p. 171-173° C. |
| N-(4-(3-Chloro-5-trifluoromethyl-2-pyridylthio)phenyl)-4,6-dichloronicotinamide | m.p. 213-215° C. |
| N-(4-(3-Chloro-5-trifluoromethyl-2-pyridyloxy)-butyn-1-yl)-4-amino-2,3-difluoro-5-nitrobenzamide | m.p. 178-180° C. |
| cis-N-(4-(3-Chloro-5-trifluoromethyl-2-pyridyloxy)-2-buten-1-yl)-4-amino-2,3-difluoro-5-nitrobenzamide | m.p. 103-105° C. |
| N-(4-(3-Chloro-5-trifluoromethyl-2-pyridyloxy)-3-(1H-pyrrol-1-yl)phenyl)-4,6-dichloronicotinamide | m.p. 171-172° C. |
| N-(4-(3-Chloro-5-trifluoromethyl-2-pyridyloxy)phenyl)-4,6-dibromonicotinamide | m.p. 220-222° C. |
| cis-N-(4-(6-Chloro-4-trifluoromethyl-2-pyridyloxy)-2-buten-1-yl)-2,3,4-trifluoro-5-nitrobenzamide | m.p. 88-89° C. |
| N-(4-(6-Chloro-4-trifluoromethyl-2-pyridyloxy)-2-butyn-1-yl)-2,3,4-trifluoro-5-nitrobenzamide | m.p. 132° C. |
| cis-N-(4-(6-Chloro-4-trifluoromethyl-2-pyridyloxy)-2-buten-1-yl)-4,6-dichloronicotinamide | m.p. 119° C. |
| N-(4-(6-Chloro-4-trifluoromethyl-2-pyridyloxy)-2-butyn-1-yl)-4,6-dichloronicotinamide | m.p. 147-148° C. |
| cis-N-(4-(6-Chloro-4-trifluoromethyl-2-pyridyloxy)-2-buten-1-yl)-2-chloro-4,5-dinitrobenzamide | m.p. 94-96° C. |
| N-(4-(6-Chloro-4-trifluoromethyl-2-pyridyloxy)-2-butyn-1-yl)-2-chloro-4,5-dinitrobenzamide | m.p. 174° C. |
| N-(4-(3-Chloro-5-trifluoromethyl-2-pyridyloxy)butyl)-2-chloro-5-nitrobenzenesulfonamide | m.p. 99-100° C. |
| N-(2-(3,5-Bistrifluoromethylbenzyloxy)ethyl)-2-chloro-5-nitrobenzenesulfonamide | m.p. 121-122° C. |
| N-(2-(3-Trifluoromethylbenzyloxy)ethyl)-2-chloro-5-nitrobenzenesulfonamide | m.p. 52-53° C. |
| N-(2-(3-Chloro-5-trifluoromethyl-2-pyridyloxy)ethyl)-2-chloro-5-nitrobenzenesulfonamide | m.p. 123-124° C. |
| N-(2-(2-Fluoro-4-trifluoromethylbenzyloxy)ethyl)-2-chloro-5-nitrobenzenesulfonamide | m.p. 133-134° C. |
| cis-N-(4-(6-Chloro-4-trifluoromethyl-2-pyridyloxy)-2-buten-1-yl)-4-amino-2-chloro-5-nitrobenzamide | m.p. 150-152° C. |
| N-(4-(6-Chloro-4-trifluoromethyl-2-pyridyloxy)-2-butyn-1-yl-4-amino-2-chloro-5-nitrobenzamide | m.p. 183-184° C. |
| N-(3-(6-Propoxy-4-trifluoromethyl-2-pyridyloxy) propyl)-2-chloro-5-nitrobenzenesulfonamide | m.p. 78-81° C. |
| N-(4-(6-Chloro-4-trifluoromethyl-2-pyridyloxy)-2-butyn-1-yl)-2-chloro-5-nitrobenzenesulfonamide | m.p. 104-105° C. |
| cis-N-(4-(3-Chloro-5-trifluoromethyl-2-pyridyloxy)-2-buten-1-yl)-2-chloro-5-nitrobenzenesulfonamide | m.p. 101-102° C. |
| cis-N-(4-(6-Chloro-4-trifluoromethyl-2-pyridyloxy)-2-buten-1-yl)-2-chloro-5-nitrobenzenesulfonamide | m.p. 89° C. |
| N-(4-(6-Chloro-4-trifluoromethyl-2-pyridyloxy)-2-butyn-1-yl)-2-chloro-5-nitrobenzenesulfonamide | m.p. 106-107° C. |
| N-(3-(3-Chloro-5-trifluoromethyl-2-pyridylthio)propyl)-2-chloro-5-nitrobenzenesulfonamide | m.p. 83-84° C. |
| N-(3-(3-Chloro-5-trifluoromethyl-2-pyridylamino)propyl)-2-chloro-5-nitrobenzenesulfonamide | m.p. 132° C. |
| N-(3-(6-Chloro-4-trifluoromethyl-2-pyridylthio)propyl)-2-chloro-5-nitrobenzenesulfonamide | m.p. 85° C. |
| N-(4-(3-Chloro-5-trifluoromethyl-2-pyridyloxy)-3-methylphenyl)-4,6-dibromonicotinamide | m.p. 198-199° C. |
| N-(3-(3-Chloro-5-trifluoromethyl-2-pyridylamino)-2,2-dimethylpropyl)-2-chloro-5-nitrobenzenesulfonamide | m.p. 58-60° C. |
| N-(3-(6-Furfuryloxy-4-trifluoromethyl-2-pyridyloxy)propyl)-2-chloro-5-nitrobenzenesulfonamide | m.p. 92-93° C. |
| N-(3-(6-Ethoxy-4-trifluoromethyl-2-pyridyloxy)propyl)-2-chloro-5-nitrobenzenesulfonamide | m.p. 58-60° C. |
| N-(4-(3-Chloro-5-trifluoromethyl-2-pyridyloxy)-3-(1-pyrrolyl)phenyl)-4,6-dibromonicotinamide | m.p. 164° C. |
| N-(3-(6-(2,2-Dimethoxyethyloxy)-4-trifluoromethyl-2-pyridyloxy)propyl)-2-chloro-5-nitrobenzenesulfonamide | m.p. 86-88° C. |
| N-(4-(3-Chloro-5-trifluoromethyl-2-pyridylamino)butyl)-2-chloro-5-nitrobenzenesulfonamide | m.p. 114° C. |
| N-(3-(6-(2-Methoxyethyloxy)-4-trifluoromethyl-2-pyridyloxy)propyl)-2-chloro-5-nitrobenzenesulfonamide | m.p. 60-61° C. |
| N-(2-(3-Chloro-5-trifluoromethyl-2-pyridylamino)ethyl)-2-chloro-5-nitrobenzenesulfonamide | m.p. 109-112° C. |
| N-(2-(2-(3-Chloro-5-trifluoromethyl-2-pyridyloxy)ethylthio)ethyl)-2-chloro-5-nitrobenzamide | m.p. 72° C. |
| N-(2-(3-Chloro-5-trifluoromethyl-2-pyridylthio)ethyl)-2-chloro-5-nitrobenzenesulfonamide | m.p. 159° C. |
| N-(3-(3-Chloro-5-trifluoromethyl-2-pyridyloxy)propyl)-4,6-dichloronicotinamide | m.p. 181-183° C. |
| N-(4-(3-Chloro-5-trifluoromethyl-2-pyridyloxy)-2-butyn-1-yl)-2-chloro-5-nitrobenzenesulfonamide | m.p. 122-123° C. |
| N-(4-(3-Chloro-5-trifluoromethyl-2-pyridyloxy)-2-butyn-1-yl)-2-fluoro-5-nitrobenzenesulfonamide | m.p. 123-126° C. |

TABLE 2-continued

| Compound | Physical properties |
|---|---|
| N-(4-(3-Chloro-5-trifluoromethyl-2-pyridyloxy)phenyl)-4-chloronicotinesulfonamide | m.p. 214-217° C. |
| N-(4-(3-Chloro-5-trifluoromethyl-2-pyridyloxy)-2-butyn-1-yl)-4-chloronicotinesulfonamide | m.p. 136° C. |
| N-(3-(3-Dimethylamino-5-trifluoromethyl-2-pyridyloxy)propyl)-2-chloro-5-nitrobenzamide | m.p. 122-123° C. |
| N-(3-(3-Dimethylamino-5-trifluoromethyl-2-pyridyloxy)propyl)-2-fluoro-5-nitrobenzamide | m.p. 90-91° C. |
| N-(3-(3-Piperidino-5-trifluoromethyl-2-pyridyloxy)propyl)-2-chloro-5-nitrobenzamide | m.p. 79-83° C. |
| N-(3-(3-Piperidino-5-trifluoromethyl-2-pyridyloxy)propyl)-2-fluoro-5-nitrobenzamide | m.p. 93-96° C. |
| N-(3-(3-Dimethylamino-5-trifluoromethyl-2-pyridylamino)propyl)-2-chloro-5-nitrobenzamide | Oil |
| N-(3-(3-Dimethylamino-5-trifluoromethyl-2-pyridylamino)propyl)-2-fluoro-5-nitrobenzamide | Oil |
| N-(3-(3-Piperidino-5-trifluoromethyl-2-pyridylamino)propyl)-2-chloro-5-nitrobenzamide | Oil |
| N-(3-(3-Piperidino-5-trifluoromethyl-2-pyridylamino) propyl)-2-fluoro-5-nitrobenzamide | Oil |
| N-(3-(6-(1-Pyrrolidinyl)-5-trifluoromethyl-2-pyridyloxy)propyl)-4,6-dichloronicotinamide | m.p. 124-127° C. |
| N-(3-(3-Cyclohexylcarbonylamino-5-trifluoromethyl-2-pyridylamino)propyl)-2-chloro-5-nitrobenzamide | m.p. 207-210° C. |
| N-(3-(3-Cyclohexylcarbonylamino-5-trifluoromethyl-2-pyridylamino)propyl)-2-fluoro-5-nitrobenzamide | m.p. 174-176° C. |
| N-(4-(6-Dimethylamino-4-trifluoromethyl-2-pyridylthio))butyl)-2-chloro-5-nitrobenzamide | m.p. 123-124° C. |
| N-(3-(6-Methylthio-4-trifluoromethyl-2-pyridyloxy)propyl)-2-chloro-5-nitrobenzamide | m.p. 106-108° C. |
| N-(4-(6-Dimethylamino-4-trifluoromethyl-2-pyridylthio))butyl)-2-chloro-5-nitrobenzenesulfonamide | m.p. 113-114° C. |
| N-(3-(6-Methylthio-4-trifluoromethyl-2-pyridyloxy)propyl)-2-chloro-5-nitrobenzenesulfonamide | m.p. 90-91° C. |
| N-(3-(3-Cyclohexylcarbonylamino-5-trifluoromethyl-2-pyridylamino)propyl)-2-chloro-5-nitrobenzenesulfonamide | m.p. 186-187° C. |
| N-(3-(3-Chloro-5-trifluoromethyl-2-pyridylamino)propyl)-2-chloro-5-nitrobenzenesulfonamide | m.p. 134-135° C. |
| N-(4-(6-Dimethylamino-4-trifluoromethyl-2-pyridylthio)butyl)-2-fluoro-5-nitrobenzamide | m.p. 88-90° C. |
| N-6-(3,5-Dimethylphenoxy)-3-pyridyl)-4-chloronicotinamide | Amorphous solid |
| N-2-(3,5-Bistrifluoromethylphenoxy)-3-pyridyl)-4-chloronicotinamide | Amorphous solid |
| N-(3-(6-Isobutoxy-4-trifluoromethyl-2-pyridyloxy)propyl)-2-chloro-5-nitrobenzamide | m.p. 97-98° C. |
| N-(3-(6-Isobutoxy-4-trifluoromethyl-2-pyridyloxy)propyl)-2-fluoro-5-nitrobenzamide | Oil |
| N-(3-(6-Tetrahydrofurfuryloxy-4-trifluoromethyl-2-pyridyloxy)propyl)-2-chloro-5-nitrobenzamide | Oil |
| N-(3-(6-Tetrahydrofurfuryloxy-4-trifluoromethyl-2-pyridyloxy)propyl)-2-fluoro-5-nitrobenzamide | Oil |
| N-(3-(6-(2-Dimethylaminoethoxy-4-trifluoromethyl-2-pyridyloxy)propyl)-2-chloro-5-nitrobenzamide | m.p. 84-86° C. |
| N-(3-(6-Cyclopentyloxy-4-trifluoromethyl-2-pyridyloxy)propyl)-2-chloro-5-nitrobenzamide | m.p. 80-81° C. |
| N-(3-(6-Cyclopentyloxy-4-trifluoromethyl-2-pyridyloxy)propyl)-2-fluoro-5-nitrobenzamide | Oil |
| N-(3-(6-Cyclopentylmethoxy-4-trifluoromethyl-2-pyridyloxy)propyl)-2-chloro-5-nitrobenzamide | m.p. 90-93° C. |
| N-(3-(6-Cyclopentylmethoxy-4-trifluoromethyl-2-pyridyloxy)propyl)-2-fluoro-5-nitrobenzamide | Oil |
| N-(3-(6-Furfuryloxy-4-trifluoromethyl-2-pyridyloxy)propyl)-2-chloro-5-nitrobenzamide | m.p. 137-138° C. |
| N-(3-(6-Furfuryloxy-4-trifluoromethyl-2-pyridyloxy)propyl)-2-fluoro-5-nitrobenzamide | m.p. 109-111° C. |
| N-(3-(3-Chloro-5-trifluoromethyl-2-pyridyloxy)propyl)-2-chloro-5-nitrobenzenesulfonamide | m.p. 106-107° C. |
| N-(3-(6-Chloro-4-trifluoromethyl-2-pyridyloxy)propyl)-2-chloro-5-nitrobenzenesulfonamide | Oil |
| N-(3-(4,6-Dimethoxy-2-pyrimidinyloxy)propyl)-2-chloro-5-nitrobenzamide | m.p. 142-146° C. |
| N-(3-(1,3-Dimethyl-5-pyrazolyloxy)propyl)-2-chloro-5-nitrobenzamide | Oil |
| N-(3-(2-Oxo-2H-chromen-4-yloxy)propyl)-2-chloro-5-nitrobenzamide | m.p. 185-187° C. |
| Methyl 1-(3-(2-chloro-4-nitrobenzoylamino)propyl)-1H-indole-3-carboxylate | m.p. 64-68° C. |
| N-(3-(4,6-Dimethyl-2-pyrimidinylthio)propyl)-2-chloro-5-nitrobenzamide | m.p. 138-140° C. |
| N-(3-Indol-1-ylpropyl)-2-chloro-5-nitrobenzamide | m.p. 103-106° C. |
| N-(3-Benzimidazol-1-ylpropyl)-2-chloro-5-nitrobenzamide | Oil |
| N-(3-(3,5-Dimethylpyrazol-1-yl)propyl)-2-chloro-5-nitrobenzamide | m.p. 96-98° C. |
| N-(3-(4-Methoxypyrimidin-2-yloxy)propyl)-2-chloro-5-nitrobenzamide | m.p. 85-88° C. |
| N-(3-Pyrrol-1-ylpropyl)-2-chloro-5-nitrobenzamide | m.p. 97-98° C. |
| N-(3-Benzoxazol-2-ylthiopropyl)-2-chloro-5-nitrobenzamide | m.p. 89-90° C. |
| N-(3-(Pyrazin-2-yloxy)propyl)-2-chloro-5-nitrobenzamide | m.p. 124-125° C. |
| N-(3-(Pyrazin-2-yloxy)propyl)-2-fluoro-5-nitrobenzamide | m.p. 106-107° C. |
| N-(3-(2-Oxo-benzothiazol-3-yl)propyl)-2-chloro-5-nitrobenzamide | m.p. 167-169° C. |
| N-(3-(2-Oxo-benzothiazol-3-yl)propyl)-2-fluoro-5-nitrobenzamide | m.p. 150-152° C. |
| N-(3-(4-Oxo-4H-quinazolin-3-yl)propyl)-2-chloro-5-nitrobenzamide | m.p. 176-178° C. |
| N-(3-(Benzothiazol-2-yloxy)propyl)-2-chloro-5-nitrobenzamide | m.p. 142-143° C. |

TABLE 2-continued

| Compound | Physical properties |
|---|---|
| N-(3-(Benzothiazol-2-yloxy)propyl-2-fluoro-5-nitrobenzamide | m.p. 97-98° C. |
| N-(3-(Benzothiazol-2-ylamino)propyl)-2-chloro-5-nitrobenzamide | m.p. 163-165° C. |
| N-(3-(1-tert-Butyl-5-chloro-6-oxo-1,6-dihydropyridazin-4-yloxy)propyl)-2-chloro-5-nitrobenzamide | Oil |
| N-(3-(1-tert-Butyl-5-chloro-6-oxo-1,6-dihydropyridazin-4-ylamino)propyl)-2-chloro-5-nitrobenzamide | m.p. 80-82° C. |
| N-(3-(3,5-Dichloro-2-pyridyloxy)propyl)-2-chloro-5-nitrobenzenesulfonamide | m.p. 97-98° C. |
| N-(3-Benzothiazol-2-ylthiopropyl)-2-chloro-5-nitrobenzenesulfonamide | m.p. 116-117° C. |
| N-(3-(5-Chloro-3-trifluoromethyl-2-pyridyloxy)propyl)-2-chloro-5-nitrobenzenesulfonamide | m.p. 75-76° C. |
| N-(3-(3-Trifluoromethylphenoxy)propyl)-2-chloro-5-nitrobenzenesulfonamide | m.p. 86-88° C. |
| N-(3-(4,5-Bistrifluoromethyl-2-pyridyloxy)propyl)-2-chloro-5-nitrobenzenesulfonamide | m.p. 95-96° C. |
| N-(3-(2-Fluoro-4-trifluoromethylphenoxy)propyl)-2-chloro-5-nitrobenzenesulfonamide | m.p. 108-110° C. |
| N-(3-(3,5,6-Trifluoro-2-pyridyloxy)propyl)-2-chloro-5-nitrobenzenesulfonamide | m.p. 104-106° C. |
| N-(3-(2-Trifluoromethyl-4-cyanophenoxy)propyl)-2-chloro-5-nitrobenzenesulfonamide | m.p. 98-99° C. |
| N-(3-(4-Phenylthiazol-2-ylthio)propyl)-2-chloro-5-nitrobenzenesulfonamide | m.p. 141-143° C. |
| N-(3-(3-Piperidino-5-trifluoromethyl-2-pyridyloxy)propyl)-2-chloro-5-nitrobenzenesulfonamide | m.p. 88-90° C. |
| N-(3-(3-Dimethylamino-5-trifluoromethyl-2-pyridyloxy)propyl)-2-chloro-5-nitrobenzenesulfonamide | m.p. 95-96° C. |
| N-(3-(4-Phenylthiazol-2-ylthio)propyl)-2-chloro-5-nitrobenzamide | m.p. 97-98° C. |
| N-(3-(5-Chlorobenzothiazol-2-ylthiopropyl)-2-chloro-5-nitrobenzamide | m.p. 168-170° C. |
| N-(3-(3-Morpholino-2-pyridyloxy)propyl)-2-chloro-5-nitrobenzenesulfonamide | m.p. 119-120° C. |
| N-(4-(3-Dimethylamino-5-trifluoromethyl-2-pyridyloxy)-2-butyn-1-yl)-2-chloro-5-nitrobenzenesulfonamide | m.p. 75-78° C. |

Test Example 1

(Test for Evaluation of IL-5 Production Inhibitory Effect)

Murine spleen cells were treated with anti-mouse CD3 antibody and IL-2 to induce cytokine production. The test compounds were added to the cytokine production system to evaluate their inhibitory effect. Namely, anti-mouse CD3 antibody adjusted to from 10 to 20 μg/ml with borate buffered physiological saline (pH 8.5) was pipetted into a 96-well cell culture plate in an amount of 50 μl/well and left to stand at 4° C. for 18 hours. The unreacted solution was removed, washing with Hank's buffer solution was carried out once, and IL-2 adjusted to 10 ng/ml with a RPMI liquid containing 10% fetal bovine serum (FCS) was pipetted in an amount of 50 μl/well. For the negative control group, a solution alone without anti-CD3 antibody nor IL-2 was applied. Then, the diluted solution of each of the test compounds (concentration: 10 ppm) was pipetted in an amount of 50 μl/well, and a cell suspension of $1 \times 10^7$ cells/ml, prepared from spleen of Balb/c mice (female, 7 to 10 week old) was pipetted thereinto in an amount of 100 μl/well. After cultivation in an incubator (37° C., 5% carbon dioxide gas) for from 40 to 48 hours, the culture supernatant was recovered to measure the cytokine production amount by ELISA method.

With respect to interleukin 5 (IL-5) as a cytokine, measurement was carried out by the following ELISA method. First, rat anti-mouse IL-5 antibody (Endogen Code No. MM-550C) as a primary antibody was diluted with carbonate buffer solution (pH 9.5) to 1 μg/ml, and spread in a 96 well plate (IWAKI, Code No. 3860-096) in an amount of 50 μl/well for coating at 4° C. overnight (16 to 24 hours). Then, the plate was subjected to blocking at 37° C. for 2 hours by phosphate buffered physiological saline containing 10% FCS (pH 7.2) (blocking buffer solution) (250 μl/well). The plate was washed with PBS (washing buffer) containing 0.05% Tween 20 (Nacalai Tesque, Code No. 281-51) four times, and a diluted liquid of the culture supernatant was spread in an amount of 50 μl/well, followed by incubation at room temperature for 1 hour. For preparation of a standard line, recombinant mouse IL-5 (R&D systems, Code No. 405-ML) was employed. The plate was washed with a washing buffer four times, and biotin-labeled rat anti-mouse IL-5 antibody (Pharmingen, Code No. 18062D) as a secondary antibody diluted to 0.5 μg/ml with a blocking buffer containing 0.05% Tween 20 was added thereto (50 μl/well), followed by incubation at room temperature for 1 hour. The plate was washed with a washing buffer four times, strept avidin-labeled peroxidase (ProZyme, Code No. CJ30H001) diluted 800 times with a blocking buffer containing 0.05% Tween 20 was added thereto (50 μl/well), followed by reaction at room temperature for 15 minutes. The plate was washed with a washing buffer four times, and a TNB substrate solution (SIGMA, Code No. T-8665) was added thereto in an amount of 100 μl/well for color developing for from 10 to 20 minutes. A 1M sulfuric acid solution was added thereto in an amount of 100 μl/well to terminate the reaction, and absorption (wavelength 450 nm) was measured by means of micro plate reader (SPECTRA max, Wako Pure Chemicals Industries, Ltd.). The experiment was carried out in duplicate, and the average of the cytokine production amount was obtained. From the average value, the inhibitory ratio (%) was obtained from the following formula.

$$\text{Inhibitory ratio } (\%) = \{1 - (T-N)/(P-N)\} \times 100$$

T: average value of the test compound group, N: average value of the negative control group, and P: average value of the positive control group.

As a result, Compounds Nos. 1 to 19 and the compounds listed in Table 2 showed cytokine production inhibitory activities of at least 50%, respectively.

Test Example 2

(Test for Evaluation of IFN-γ Production Inhibitory Effect)

Quantitative determination of IFN-γ in mouse spleen cell culture supernatants is carried out in the same manner as in Test Example 1, employing rat anti-mouse IFN-γ antibody (Pharmingen, Code No. 18181D) as the primary antibody, a biotin-labeled rat anti-mouse IFN-γ antibody (Pharmingen, Code No. 18112D) as the secondary antibody. For preparation of a standard line, recombinant mouse IFN-γ (GEN- ZYME, Code No. 3485) is employed. The resulting IFN-γ production inhibitory ratios (%) indicate that the compounds of the present invention have IFN-γ production inhibitory effect.

Test Example 3

(Test for Evaluation of Efficacy on Antigen (OVA)-Induced Cytokine Production in Mice)

BALB/c mice (purchased from Japan SLC, Inc., male, 5 to 8-week old) are intraperitoneally (or subcutaneously) immunized with 2 mg of an alum adjuvant (aluminum potassium sulfate, manufactured by Nacalai Tesque, No. 017-27) and 2 μg/mouse of an ovalbumin (OVA) preparation (manufactured by SIGMA, No. A-5503) and, 10 to 14 days later, immunized again intraperitoneally (or subcutaneously) with OVA 1 μg/alum 2 mg. Four days after the second immunization, 0.2 ml of 5 μg/ml OVA in physiological saline is injected into the mouse abdominal cavities to induce cytokine production and eosinophilic infiltration. After another six hours, the mice are euthanized with carbon dioxide gas, and 2 ml of 0.01 M phosphate buffered physiological saline (PBS) pH 7.2 is injected into the abdominal cavities, and after thorough abdominal massage, the abdominal perfusates are recovered. The recovered abdominal perfusates are centrifuged in a miniature cooling centrifuge at 10,000 rpm at 4° C. for 10 minutes. The supernatants are recovered and refrigerated at −80° C. until measurements. The IL-5 and INF-γ concentrations are measured by ELISA in the same manners as in Test Examples 1 and 2. The test compounds are administered subcutaneously or orally 1 hour before the last induction by intraperitoneal injection of OVA. The efficacy is expressed as an inhibitory ratio (%) based on the control solvent. As a result, the compounds of the present invention turn out to have efficacy.

Test Example 4

(Test for Evaluation of Efficacy on Antigen (OVA)-Induced Eosinophilic Infiltration in Mice)

The procedure in Test Example 3 is followed to recover the abdominal perfusates 24 hours after the last induction by OVA, and refrigerated at −80° C. until measurements. The eusinophil counts in the abdominal perfusates are determined by the eosinophil peroxidase (EPO) assay of Strath et al., Journal of Immunological Methods, Vol. 83, pp. 209-215, 1985, with some modifications. Namely, 0.1 mL of 0.05 M Tris-HCL (pH 8.0) containing 3 mM o-phenylenediamine, 0.1% TritonX-100 and 8.8 mM hydrogen peroxide as a substrate buffer is mixed with 0.05 mL of a test liquid diluted with PBS, and after 30 minutes of reaction at room temperature, 0.05 mL of 4 M sulfuric acid solution is added to terminate the enzymatic reaction. The absorption A1 at a measurement wavelength of 492 nm is measured with a microplate reader. In parallel, the same procedure is done with a substrate buffer further containing 10 mM 3-amino-1,2,4-triazol (AMT) as an EPO inhibitor, and the absorption A2 is measured. The absorption (A1-A2) attributable to eosinophils is calculated. The test compounds are administered subcutaneously or orally 1 hour before the last induction by intraperitoneal injection of OVA. The efficacy is expressed as an inhibitory ratio (%) based on the control solvent. As a result, the compounds of the present invention turn out to have efficacy.

The entire disclosure of Japanese Patent Application No. 2004-040444 filed on Feb. 17, 2003 including specification, claims and summary is incorporated herein by reference in its entirety.

The invention claimed is:

1. A thioamide compound represented by formula (I) or a salt thereof:

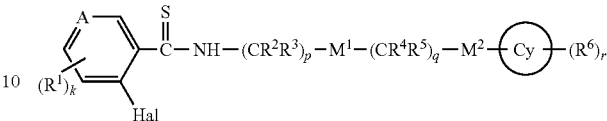

wherein

A is a nitrogen atom, N-oxide, C—$NO_2$ or C—CN;

Hal is a halogen atom;

$M^1$ is an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted, an oxygen atom, a sulfur atom, SO or $SO_2$;

$M^2$ is an amino group which may be substituted, an oxygen atom, a sulfur atom or a single bond;

$R^1$ is a halogen atom, a cyano group, a nitro group, an alkyl group which may be substituted, an alkoxy group which may be substituted, an alkylthio group which may be substituted, an amino group which may be substituted or a heterocyclic group which may be substituted;

each of $R^2$, $R^3$, $R^4$ and $R^5$ is independently a hydrogen atom, an alkyl group which may be substituted, a cyano group or an alkyloxycarbonyl group; $R^6$ is a halogen atom, a cyano group, a nitro group, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, an amino group which may be substituted or B-Q (wherein B is a carbonyl group, a carbonyloxy group, an oxycarbonyl group, an oxygen atom, a sulfur atom, SO or $SO_2$; and Q is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted or an amino group which may be substituted);

Cy is a cycloalkyl group, a cycloalkenyl group, an aryl group or a heterocyclic group;

each of k, p and q is independently an integer of from 0 to 3; and r is an integer of from 0 to 5.

2. The compound according to claim 1, wherein p and q are 0, or a salt thereof.

3. A pharmaceutical composition comprising the compound according to claim 1 and a pharmaceutically acceptable carrier.

4. A pharmaceutical composition comprising the compound according to claim 2 and a pharmaceutically acceptable carrier.

* * * * *